US008670941B2

(12) United States Patent
Fonteh et al.

(10) Patent No.: US 8,670,941 B2
(45) Date of Patent: Mar. 11, 2014

(54) METHODS OF DETERMINING LEVELS OF FREE AMINO ACIDS AND DIPEPTIDES AND DIAGNOSING ALZHEIMER'S DISEASE

(75) Inventors: Alfred N. Fonteh, Quartz Hill, CA (US); Michael G. Harrington, La Canada, CA (US)

(73) Assignee: Huntington Medical Research Institutes, Pasadena, CA (US)

(*) Notice: Subject to any disclaimer, the term of this patent is extended or adjusted under 35 U.S.C. 154(b) by 711 days.

(21) Appl. No.: 12/377,765

(22) PCT Filed: Aug. 17, 2007

(86) PCT No.: PCT/US2007/018297
§ 371 (c)(1),
(2), (4) Date: Jan. 4, 2011

(87) PCT Pub. No.: WO2008/021515
PCT Pub. Date: Feb. 21, 2008

(65) Prior Publication Data
US 2011/0097736 A1 Apr. 28, 2011

Related U.S. Application Data

(60) Provisional application No. 60/838,606, filed on Aug. 18, 2006.

(51) Int. Cl.
*A61B 5/145* (2006.01)
*G01N 33/48* (2006.01)
*G01N 33/49* (2006.01)
*B01D 15/08* (2006.01)

(52) U.S. Cl.
USPC ............................................ 702/19; 530/417

(58) Field of Classification Search
None
See application file for complete search history.

(56) References Cited

U.S. PATENT DOCUMENTS 7,009,174 B2    3/2006 Le Blanc

OTHER PUBLICATIONS

Molina et al., J Neural Transmission, 105:279-286, 1998.*
Molina et al., Cerebrospinal fluid levels of non-neurotransmitter amino acids in patients with Alzheimer's disease, J Neural Transm 105: 279-286, 1998.*
Storga et al., Monoaminergic neurotransmitters, their precursors and metabolites in brains of Alzheimer patients, Neurosci Lett 203: 29-32, 1996.*
Pomara et al., Glutamate and other CSF amino acids in Alzheimer's disease, Am J Psychiatry 149: 251-254, 1992.*
Coon et al., Tandem Mass Spectrometry for Peptide and Protein Sequence Analysis, BioTechniques 38(4):519-523, 2005.*
Hipkiss AR, Carnosine, a protective, anti-ageing peptide?, International J of Biochem and Cell Biol., 30:863-868, 1998.*
Ducci et al., Polish J Vet Sci, 9(3):159-163, 2006.*
Bowers LD, Clin Chem., 35/7:1282-1287, 1989.*
Bourcier, S. et al. (2006). "Detection of 28 Neurotransmitters And Related Compounds In Biological Fluids by Liquid Chromatography/Tandem Mass Spectrometry," *Rapid Commun. Mass Spectrom.* 20(9):1405-1421.
Cellar, N.A. et al. (Nov. 1, 2005). "Microfluidic Chip For Low-Flow Push-Pull Perfusion Sampling In Vivo With On-Line Analysis of Amino Acids," *Anal. Chem.* 77:7067-7073.
Chapman, P.F. et al. (May 2001). "Genes, Models and Alzheimer's Disease," *Trends in Genet.* 17(5):254-261.
Cummings, J.L. et al. (Jul. 1998). "Alzheimer's Disease: Etiologies, Pathophysiology, Cognitive Reserve, And Treatment Opportunities," *Neurology* 51(1 Suppl. 1):S65-S67.
Doraiswamy, P.M. et al. (Mar. 2002). "Prevalence And Impact of Medical Comorbidity in Alzheimer's Disease," *J. Gerontol. Bio. Sci. Med. Sci.* 57A(3):M173-M177.
Durkin, T.A. et al. (Jun. 24, 1988). "High-Performance Liquid Chromatographic Analysis of Neurotransmitter Amino Acids In Brain," *J. Chromatogr.* 428(1):9-15.
Fonteh, A.N. et al. (Feb. 2007). "Free Amino Acid and Dipeptide Changes in the Body Fluids from Alzheimer's Disease Subjects," *Amino Acids* 32(2):213-224.
Harrington, M.G. et al. (Jul./Aug. 2006). "Cerebrospinal Fluid Sodium Increases In Migraine," *Headache* 46(7):1128-1135.
Holtzman, D.M. et al. (Mar. 14, 2000). "Apolipoprotein E Isoform-Dependent Amyloid Deposition and Neuritic Degeneration In A Mouse Model of Alzheimer's Disease," *PNAS* 97(6):2892-2897.
Husek, P. (Mar. 25, 1991). "Amino Acid Derivatization And Analysis In Five Minutes," *FEBS Letters* 280(2):354-356.
Husek, P. (Oct. 9, 1998). "Chloroformates In Gas Chromatography As General Purpose Derivatizing Agents," *J. Chromatogr. B.* 717(1-2):57-91.
International Search Report mailed on Apr. 9, 2008, for PCT Application PCT/US2007/018297, filed on Aug. 17, 2007, 5 pages.
Jansen, E.E.W. et al. (Jan. 18, 2006). "A Novel, Quantitative Assay For Homocarnosine In Cerebrospinal Fluid Using Stable-Isotope Dilution Liquid Chromatography-Tandem Mass Spectrometry," *J. Chromatography* 830(2):196-200.
Jiménez-Jiménez, F.J. et al. (1998). "Neurotransmitter Amino Acids in Cerebrospinal Fluid of Patients with Alzheimer's Disease," *Journal of Neural Transmission* 105(2-3):269-277.
Martinez, M. et al. (1993). "Amino Acid Concentrations in Cerebrospinal Fluid and Serum in Alzheimer's Disease and Vascular Dementia," *Journal of Neural Transmission (Parkinson's Disease and Dementia Section)* 6(1):1-9.
Molina, J.A. et al. (1998). "Cerebrospinal Fluid Levels of Non-Neurotransmitter Amino Acids in Patients with Alzheimer's Disease," *Journal of Neural Transmission* 105(2-3):279-286.

(Continued)

*Primary Examiner* — Daniel E Kolker
*Assistant Examiner* — Stacey N MacFarlane
(74) *Attorney, Agent, or Firm* — Morrison & Foerster LLP

(57) ABSTRACT

Provided herein are methods of diagnosing Alzheimer's disease ("AD") based on characteristic changes of the levels of certain free amino acids or dipeptides (collectively termed as "AD diagnosis markers") in the body fluid sample of an individual, carnosine synthesis activities in the plasma, and dopamine synthesis activities in the plasma. Also provided are methods of simultaneously determining the levels of at least two free amino acids or dipeptides in the biological fluid sample of an individual.

22 Claims, 15 Drawing Sheets

(56) References Cited

OTHER PUBLICATIONS

Petritis, K. et al. (Oct. 27, 2000). "Parameter Optimization For The Analysis of Underivatized Protein Amino Acids By Liquid Chromatography And Ionspray Tandem Mass Spectrometry," *J. Chromatogr. A.* 896(1-2):253-263.

Piraud, M. et al. (2005, e-pub. Oct. 18, 2005). "A New Reversed-Phase Liquid Chromatographic/Tandem Mass Spectrometric Method For Analysis of Underivatised Amino Acids: Evaluation For The Diagnosis And The Management of Inherited Disorders of Amino Acid Metabolism," *Rapid Commun. Mass Spectrom.* 19(22):3287-3297.

Schwarz, E.L. et al. (Apr. 2005). "Analysis of Plasma Amino Acids By HPLC With Photodiode Array And Fluorescence Detection," *Clin. Chim. Acta* 354(1-2):83-90.

Written Opinion of the International Searching Authority mailed on Apr. 9, 2008, for PCT Application PCT/US2007/018297, filed on Aug. 17, 2007, 10 pages.

Yasuda, M. et al. (1993). "Peptide Histidine Methionine in Cerebrospinal Fluid of Patients with Senile Dementia of the Alzheimer Type," *Japanese Journal of Psychiatry and Neurology* 47(1):85-90.

* cited by examiner

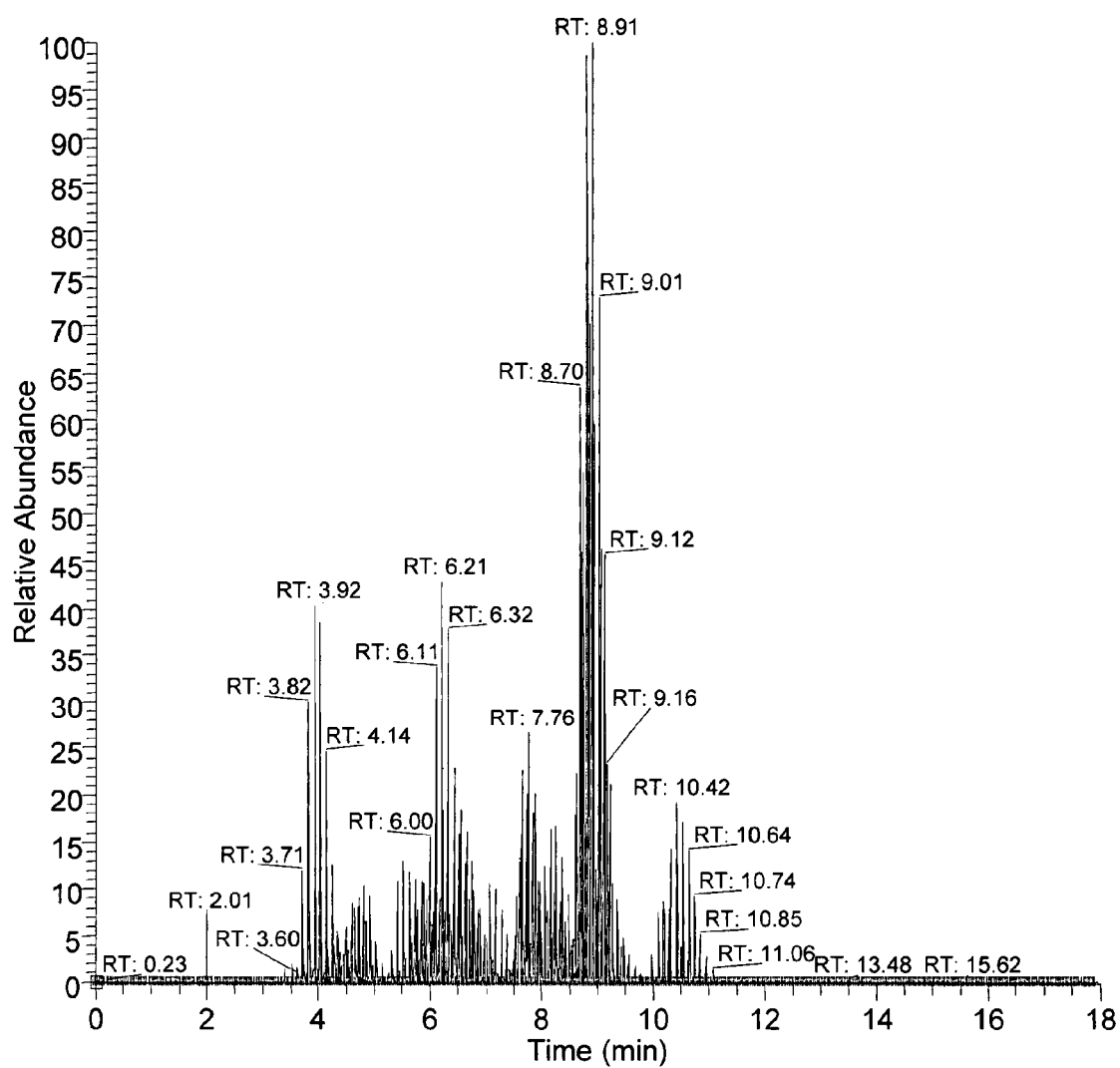
FIGURE 1A- Total ion current

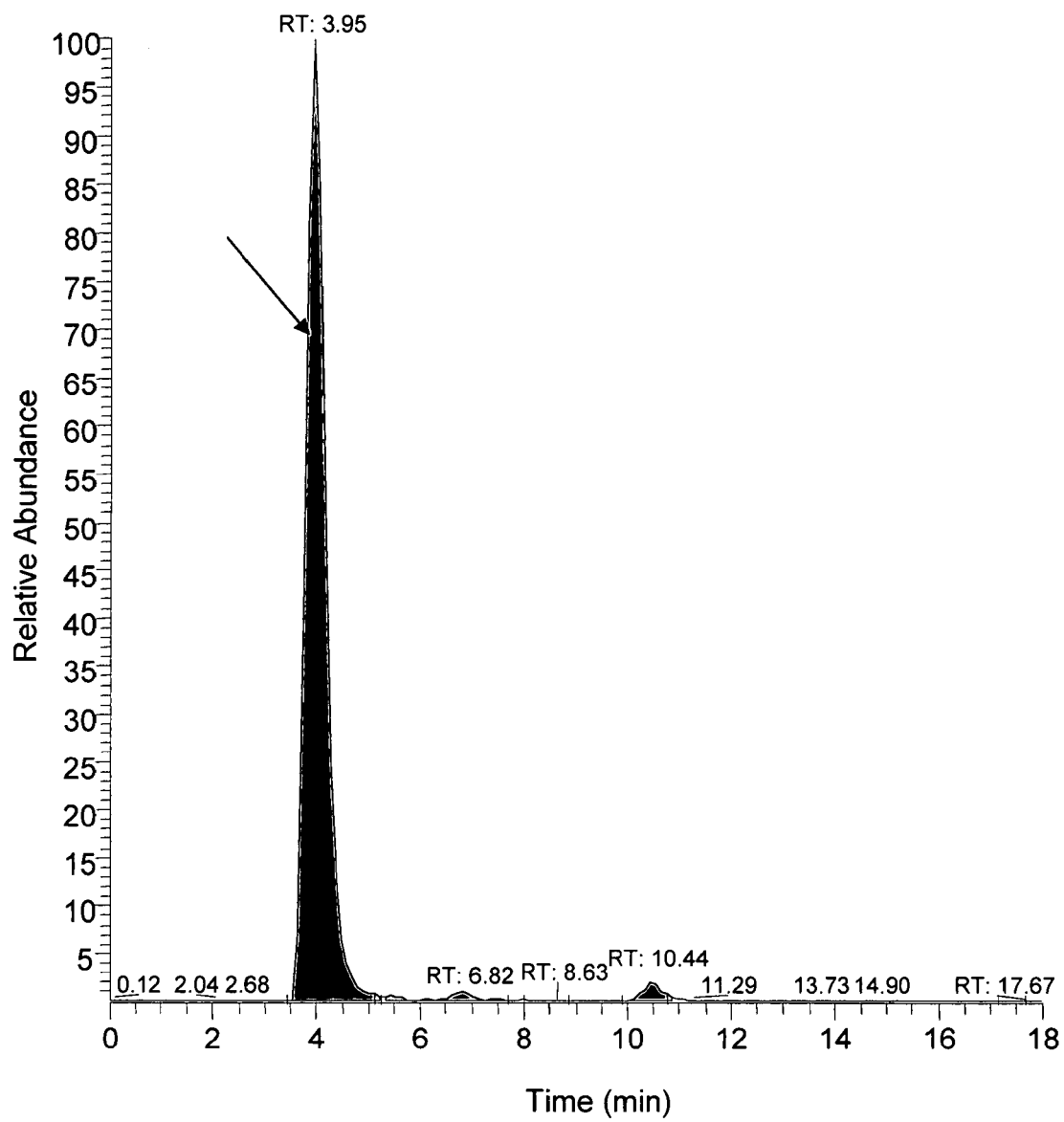
FIGURE 1B- Homoarginine

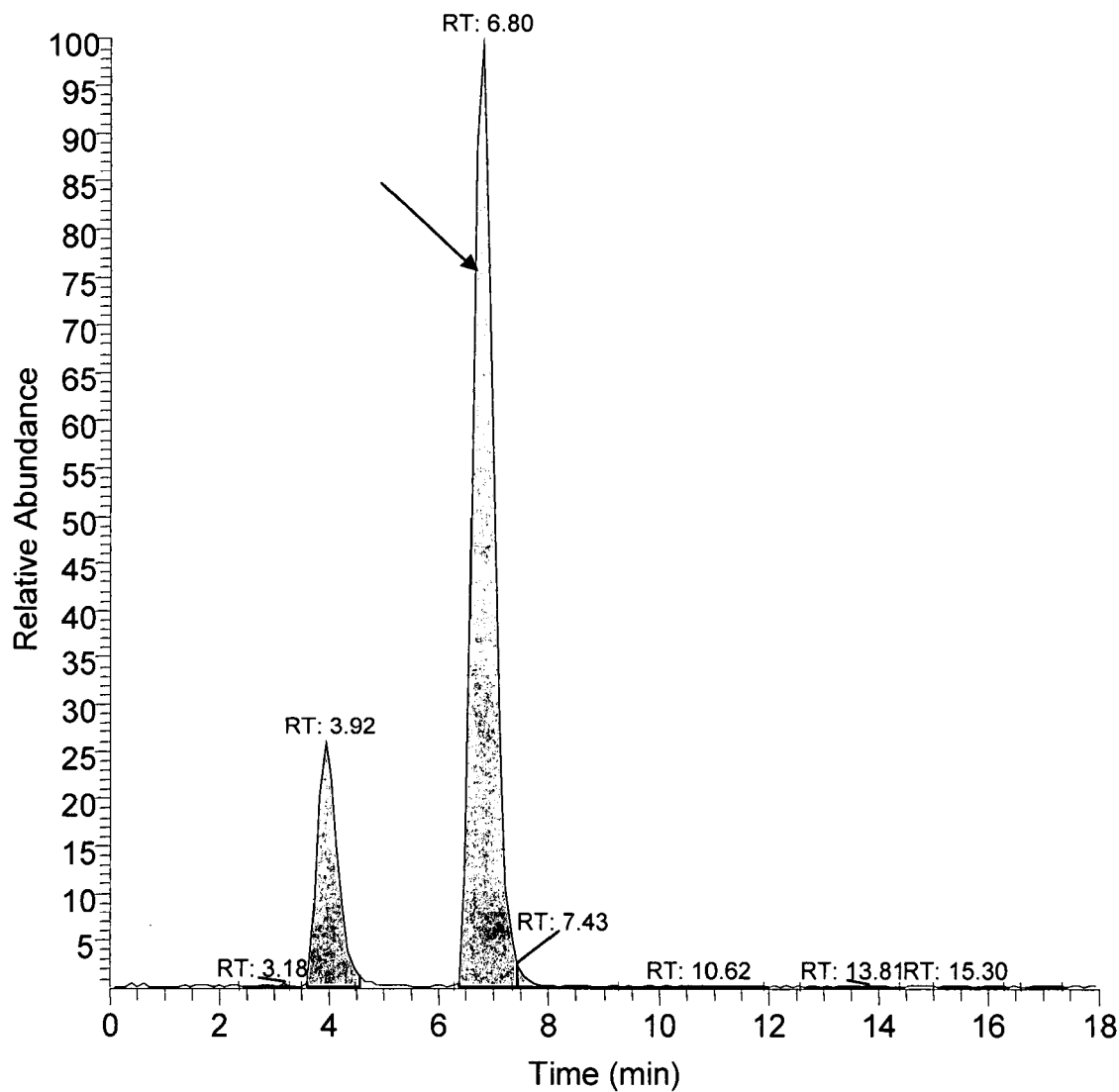
FIGURE 1C- [15N]-Glutamic acid

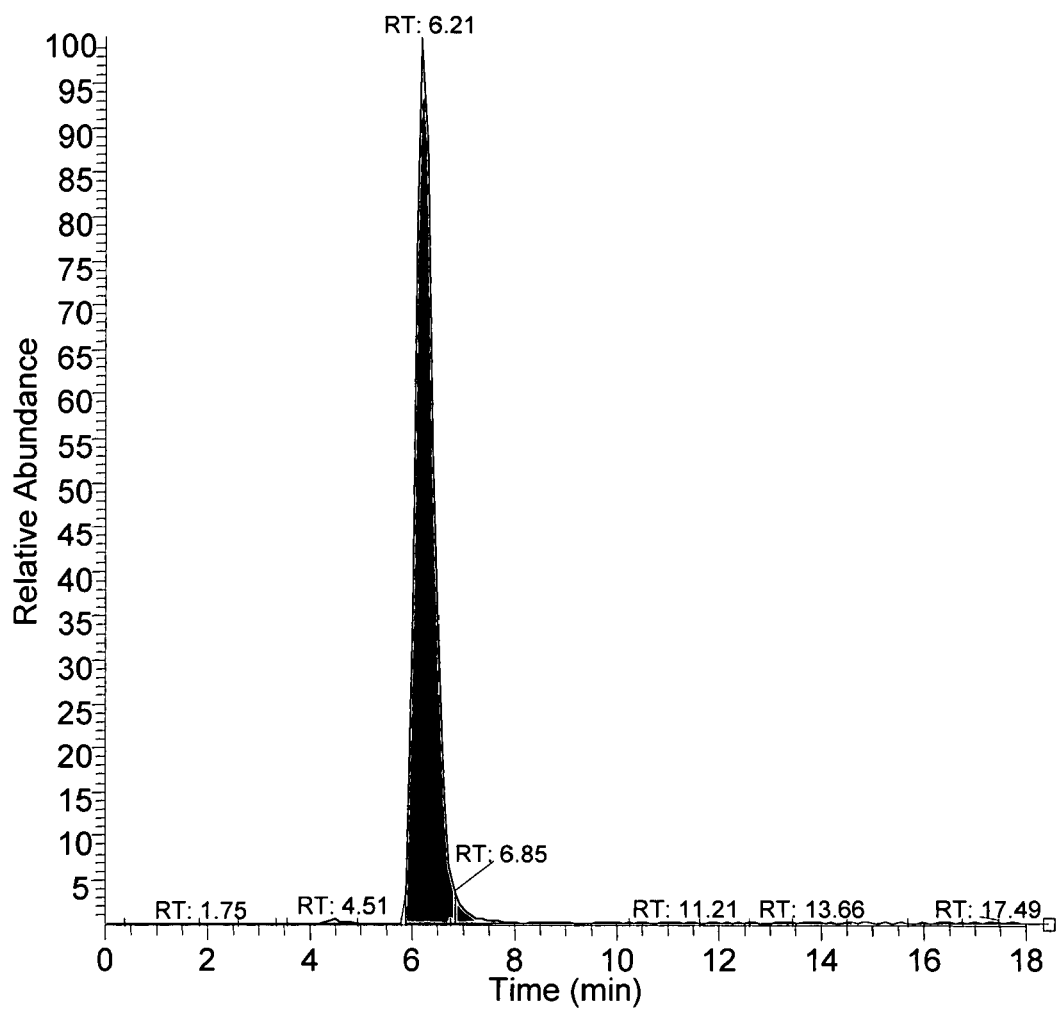
FIGURE 1D- [2H3]-Methionine

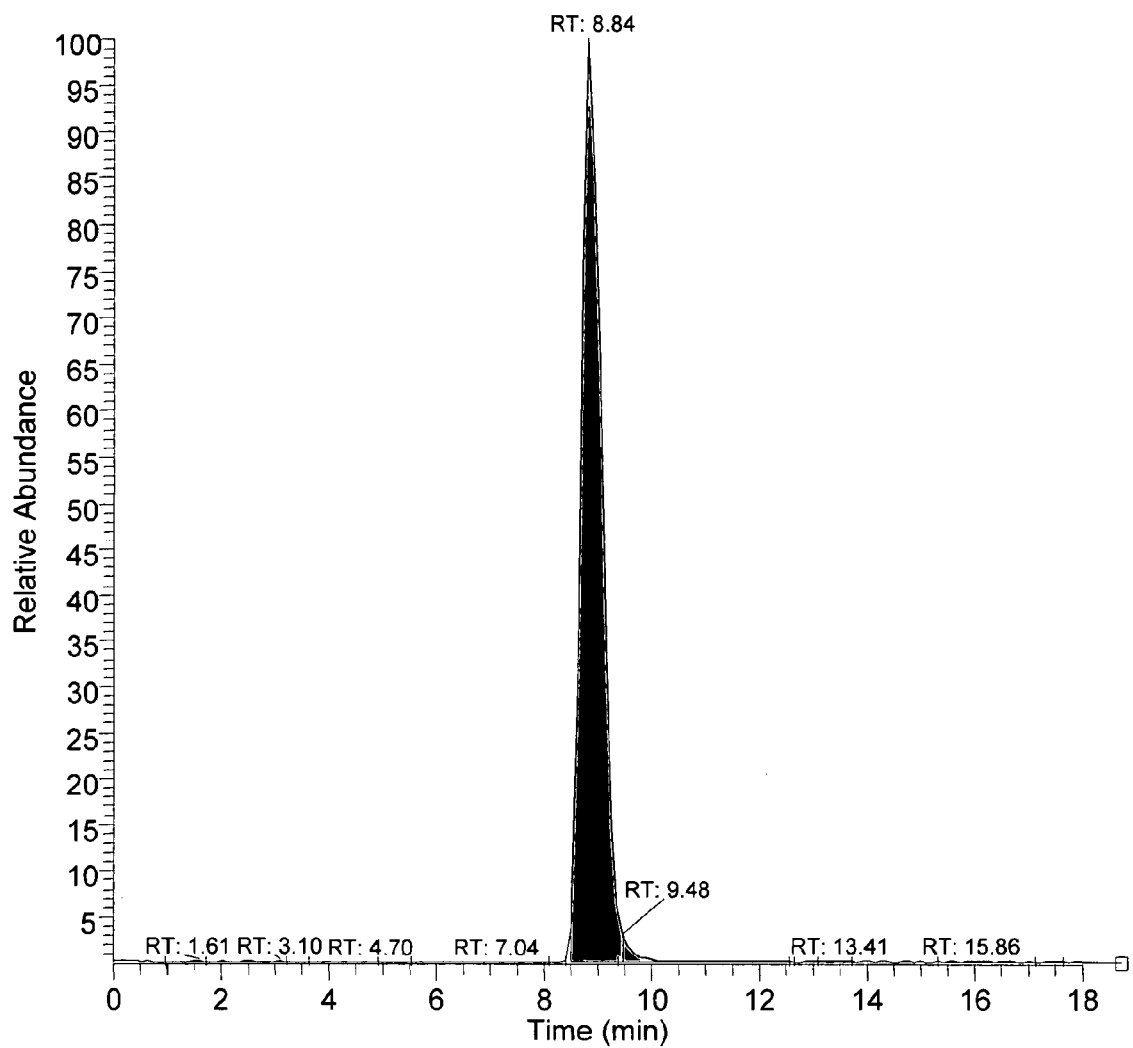
FIGURE 1E- Homophenylalanine

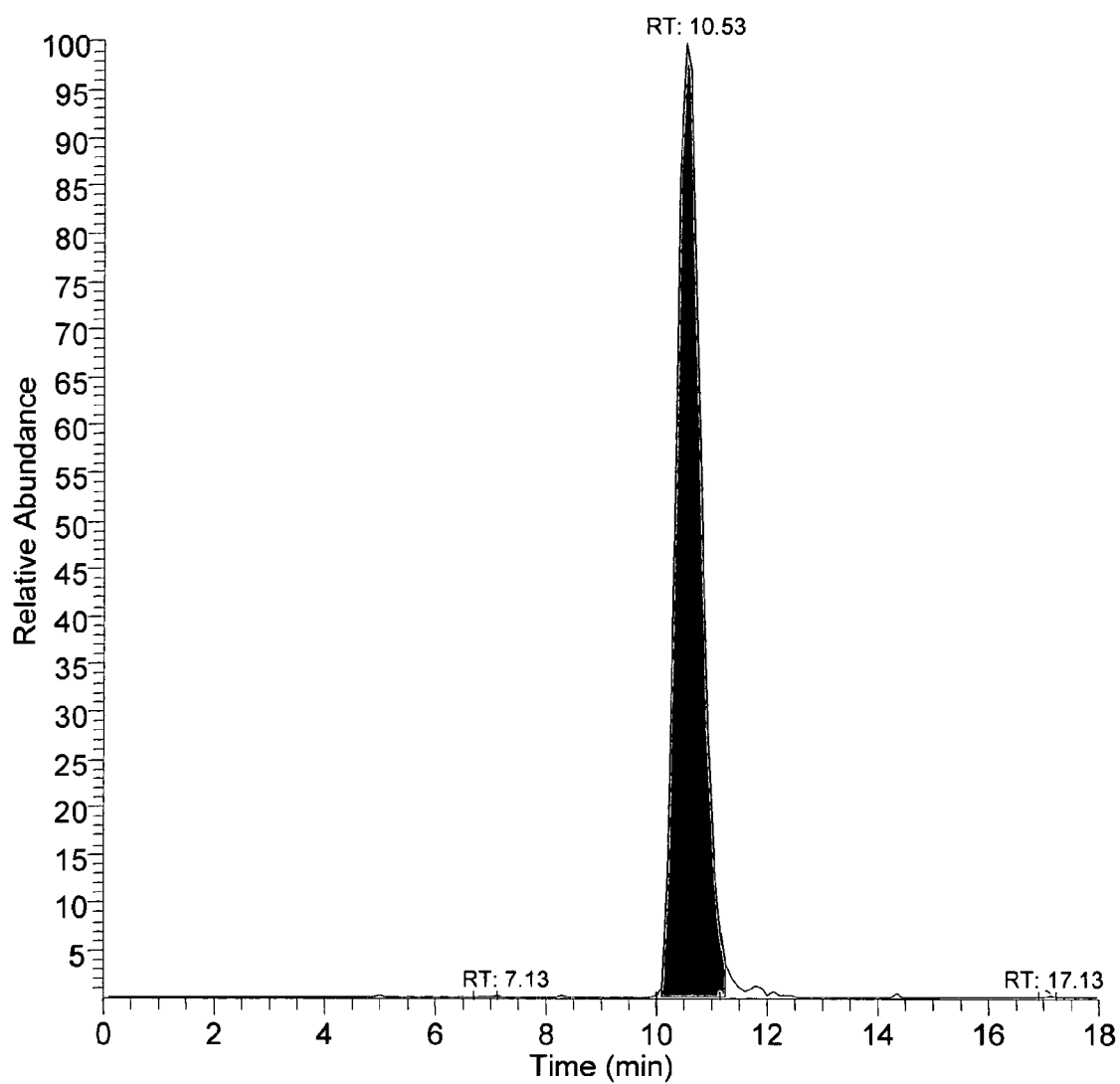

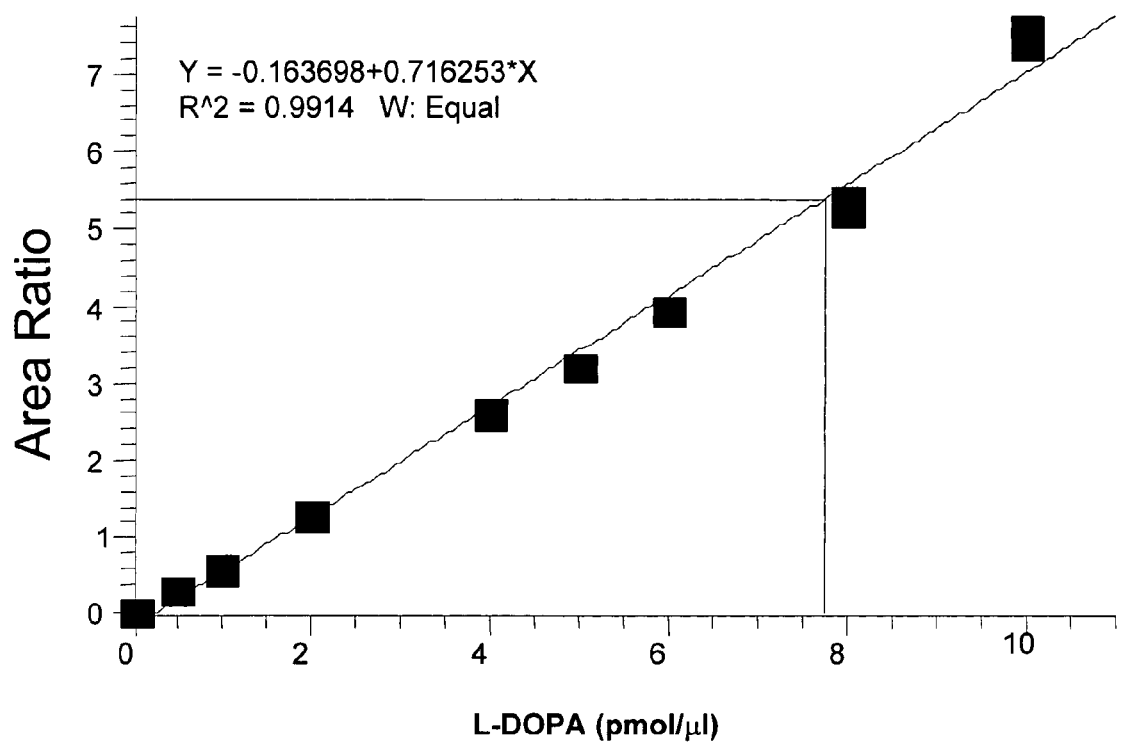
FIGURE 1G- Standard curve for L_DOPA

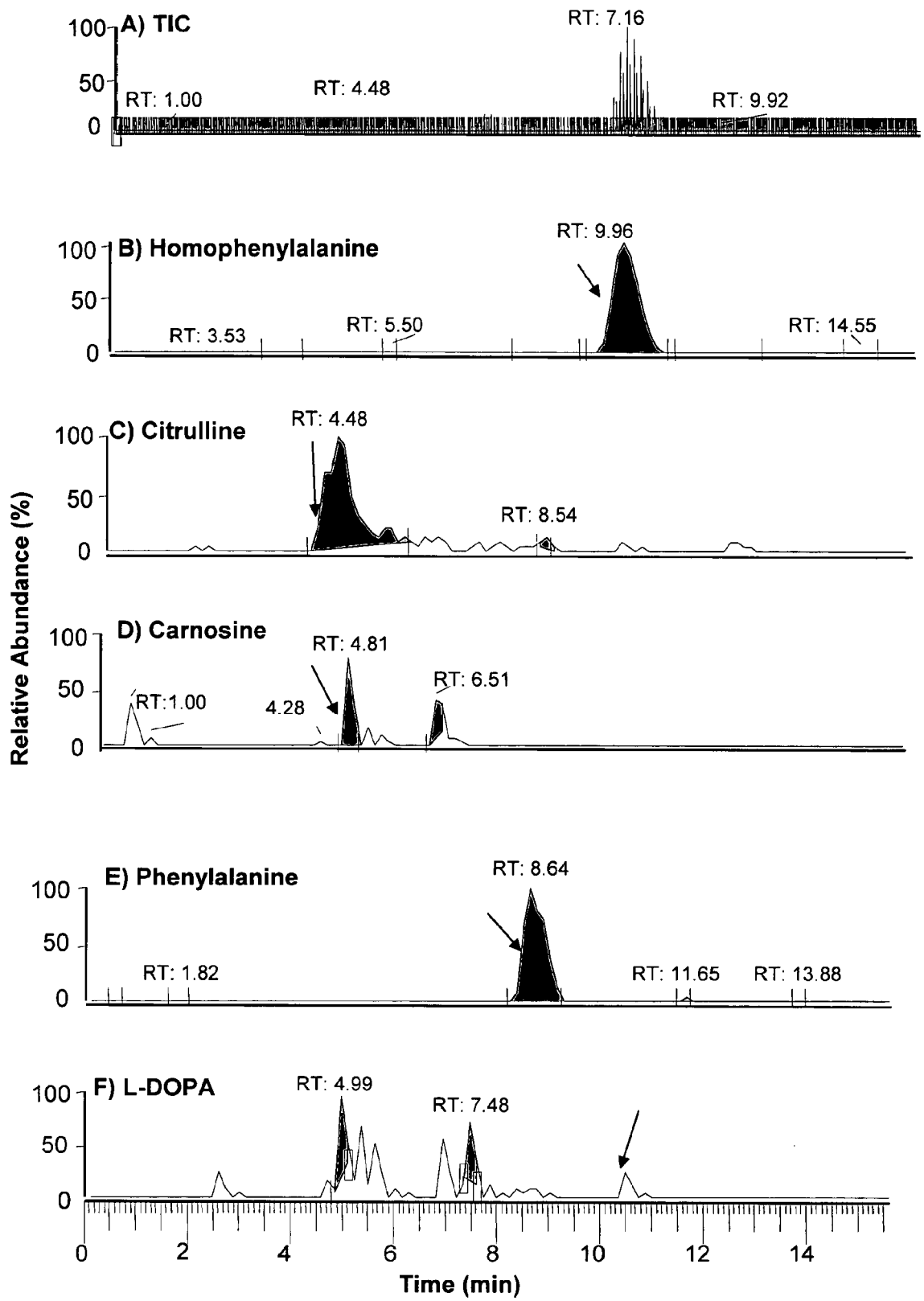
FIGURE 2- CSF

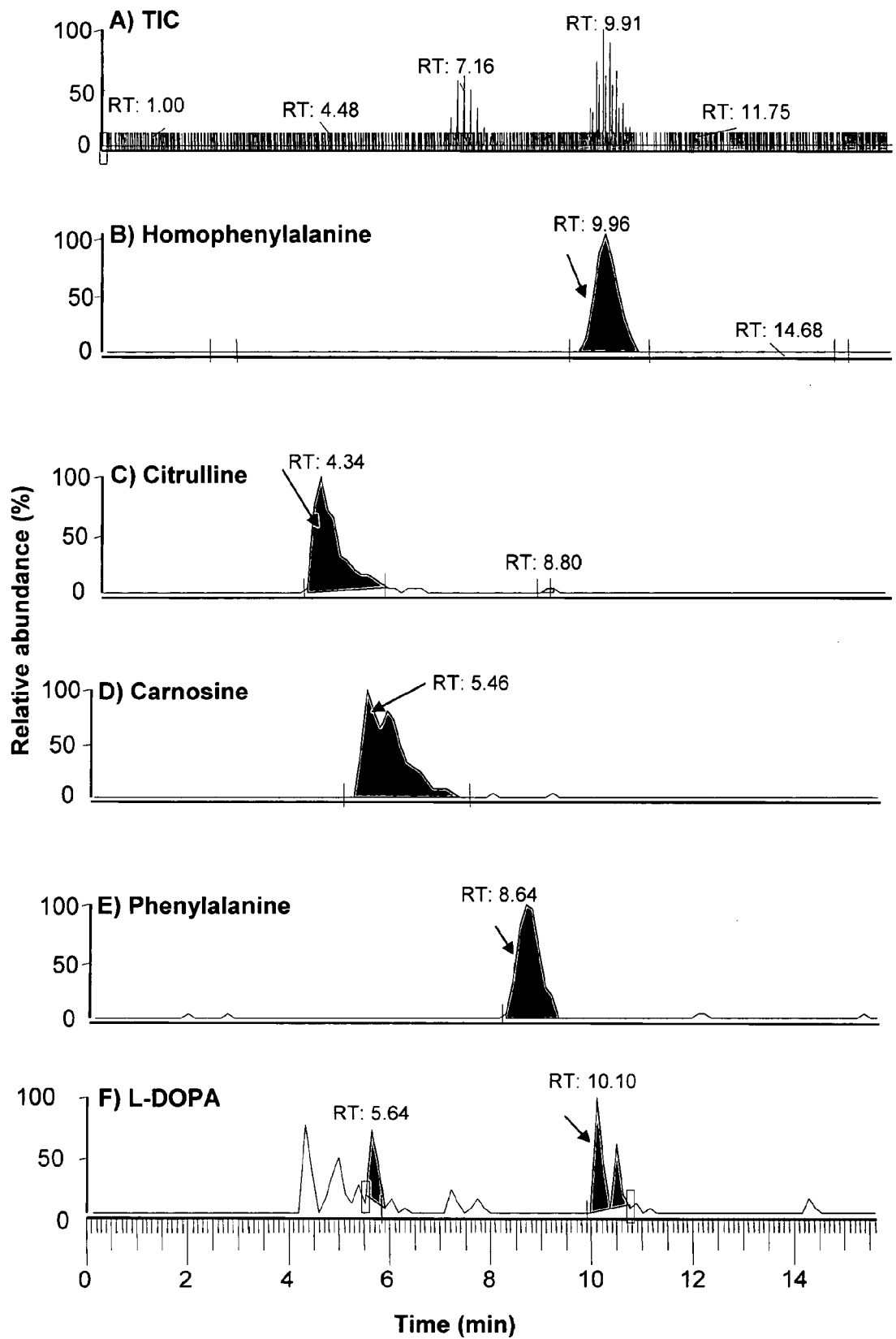
FIGURE 3- Plasma

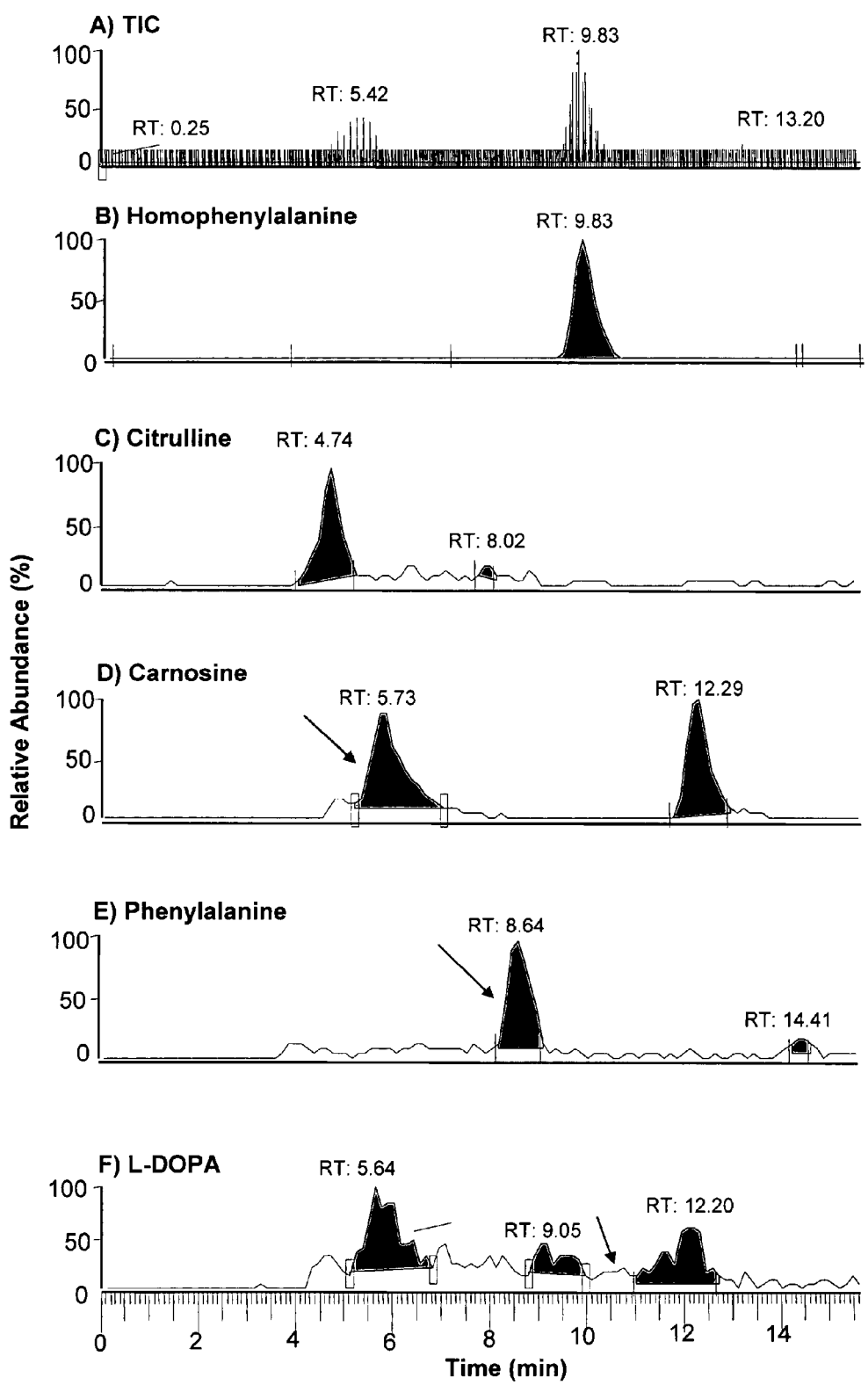
FIGURE 4- URINE

METHODS OF DETERMINING LEVELS OF FREE AMINO ACIDS AND DIPEPTIDES AND DIAGNOSING ALZHEIMER'S DISEASE

CROSS-REFERENCE TO RELATED APPLICATIONS

This application is a National Phase filing under 35 U.S.C. §371 of International Application No. PCT/US2007/018297 having an international filing date of Aug. 17, 2007, which claims the benefit of U.S. Provisional Application No. 60/838,606, filed Aug. 18, 2006, each of which are incorporated by reference in their entirety.

TECHNICAL FIELD

This application pertains to methods of diagnosing Alzheimer's disease based on the levels of certain free amino acids or dipeptides. The application also pertains to methods of determining levels of free amino acids and dipeptides using liquid chromatography tandem mass spectrometry methods.

BACKGROUND

Alzheimer's disease ("AD") is a neurodegenerative disorder with an estimated worldwide prevalence of over eighteen million people, and is predicted to increase with an increasing elderly population. AD is characterized by cognitive deficits and memory impairment, and there is currently no cure for this disease. Several genetic, age, demographic and environmental factors are linked to AD pathophysiology. Chapman et al., 2001, *Trends in Genet.* 17, 254-261; Cummings et al., 1998, *Neurology,* 51, S2-17; Doraiswamy et al., 2002, *Bio. Sci. Med. Sci.,* 57, M173-M177. Two pathological characteristics are observed in AD patients at autopsy: extracellular plaques and intracellular tangles in the hippocampus, cerebral cortex, and other areas of the brain essential for cognitive function. Plaques are formed mostly from the deposition of amyloid beta ("Aβ"), a peptide derived from amyloid precursor protein ("APP"). Filamentous tangles are formed from paired helical filaments composed of neurofilament and hyperphosphorylated tau protein, a microtubule-associated protein.

The main clinical feature of AD is a progressive cognitive decline leading to memory loss. Memory dysfunction involves impairment of learning new information which is often characterized as short-term memory loss. In the early (mild) and moderate stages of the illness, recall of remote well-learned material may appear to be preserved, but new information cannot be adequately incorporated into memory. Disorientation to time is also closely related to memory disturbance.

Language impairments are also a prominent part of AD. These are often manifest first as word finding difficulty in spontaneous speech. The language of the AD patient is often vague, lacking in specifics and may have increased automatic phrases and clichés. Difficulty in naming everyday objects is often prominent. Complex deficits in visual function are present in many AD patients, as are other focal cognitive deficits such as apraxia, acalculia and left-right disorientation. Impairments of judgment and problem solving are frequently seen.

Non-cognitive or behavioral symptoms are also common in AD. Personality changes are commonly reported and range from progressive passivity to marked agitation. Patients may exhibit changes such as decreased expressions of affection, depressive symptoms, anxiety, and psychosis. In some cases, personality changes may predate cognitive abnormality.

Currently, the primary method of diagnosing AD involves taking detailed patient histories, administering memory and psychological tests, and ruling out other explanations for memory loss, including temporary (e.g., depression or vitamin B12 deficiency) or permanent (e.g., stroke) conditions. Under this approach, AD cannot be conclusively diagnosed until after death, when autopsy reveals the disease's characteristic amyloid plaques and neurofibrillary tangles in a patient's brain. In addition, clinical diagnostic procedures are only helpful after patients have begun displaying significant, abnormal memory loss or personality changes. By then, a patient has likely had AD for years. There is therefore a need for other methods of diagnosing and aiding diagnosis of AD.

Mass spectrometers are often coupled with chromatography systems in order to identify and characterize eluting species from a test sample. In such a coupled system, the eluting solvent is ionized and a series of mass spectrograms are obtained. In some cases, liquid chromatography is coupled with tandem mass spectrometry (LCMS$^2$) for better analysis of test samples. See, e.g., U.S. Pat. No. 7,009,174; Jansen et al., *J. Chromatography,* 830:196-200 (2006).

The disclosures of all publications, patents, patent applications and published patent applications referred to herein are hereby incorporated herein by reference in their entirety.

BRIEF SUMMARY OF THE INVENTION

The invention in one aspect provides a method of diagnosing Alzheimer's disease ("AD") in an individual, comprising: a) comparing the level of at least one AD diagnosis marker in a body fluid sample (such as plasma, urine, and CSF) from the individual with a reference level, and b) determining whether the individual has AD based on a characteristic change in the level of at least one AD diagnosis biomarker, wherein the AD diagnosis marker is a free amino acid or dipeptide selected from the group consisting of: an imidazole-containing free amino acid or dipeptide having antioxidant properties, an aromatic-containing free amino acid that is a neurotransmitter, a free amino acid or dipeptide associated with urea metabolism or detoxification and NO formation, a glutamate-derived free amino acid or dipeptide, and an asparate or serine-derived free amino acid. In some embodiments, there is provided a method of providing information for diagnosis of AD in an individual comprising: a) determining the level of at least one AD diagnosis marker in the body fluid sample of the individual, and b) providing information about the level of at least one AD diagnosis marker for diagnosis of AD, wherein the level of the at least one AD diagnosis marker is used as basis for diagnosing AD, wherein a characteristic change in the level of the at least one AD diagnosis biomarker is indicative of AD, and wherein the AD diagnosis marker is a free amino acid or dipeptide selected from the group consisting of: an imidazole-containing free amino acid or dipeptide having antioxidant properties, an aromatic-containing free amino acid that is a neurotransmitter, a free amino acid or dipeptide associated with urea metabolism or detoxification and NO formation, a glutamate-derived free amino acid or dipeptide, and an asparate or serine-derived free amino acid. In some embodiments, the levels of the AD diagnosis markers are determined by liquid chromatography tandem mass spectrometry ("LCMS$^2$") method.

In some embodiments, the invention provides a method of aiding diagnosis of Alzheimer's disease ("AD") in an individual, comprising: a) comparing the level of at least one AD diagnosis marker in a body fluid sample (such as plasma, urine, and CSF) from the individual with a reference level, and b) determining whether the individual has AD based on a characteristic change in the level of at least one AD diagnosis biomarker and at least one other method of diagnosing AD, wherein the AD diagnosis marker is a free amino acid or dipeptide selected from the group consisting of: an imidazole-containing free amino acid or dipeptide having antioxidant properties, an aromatic-containing free amino acid that is a neurotransmitter, a free amino acid or dipeptide associated with urea metabolism or detoxification and NO formation, a glutamate-derived free amino acid or dipeptide, and an asparate or serine-derived free amino acid. In some embodiments, there is provided a method of providing information for aiding diagnosis of AD in an individual comprising: a) determining the level of at least one AD diagnosis marker in the body fluid sample of the individual, and b) providing information about the level of at least one AD diagnosis marker for diagnosis of AD, wherein the level of the at least one AD diagnosis marker is used as basis for diagnosing AD, wherein a characteristic change in the level of the at least one AD diagnosis biomarker is suggestive of AD, and wherein the AD diagnosis marker is a free amino acid or dipeptide selected from the group consisting of: an imidazole-containing free amino acid or dipeptide having antioxidant properties, an aromatic-containing free amino acid that is a neurotransmitter, a free amino acid or dipeptide associated with urea metabolism or detoxification and NO formation, a glutamate-derived free amino acid or dipeptide, and an asparate or serine-derived free amino acid. In some embodiments, the levels of the AD diagnosis markers are determined by LCMS$^2$ method.

In some embodiments, the body fluid sample is cerebrospinal fluid (CSF). In some embodiments, the body fluid sample is plasma. In some embodiments, the body fluid sample is urine. In some embodiments, the body fluid sample is selected from the group consisting of CSF, plasma, and urine. In some embodiments, the body fluid sample is a peripheral body fluid (including plasma and urine).

In some embodiments, at least one AD diagnosis marker is an imidazole-containing free amino acid or dipeptide having antioxidant properties, such as an imidazole-containing free amino acid or dipeptide selected from the group consisting of histidine, 1-methyl-histidine, 3-methyl-histidine, carnosine, and anserine. In some embodiments, the imidazole-containing free amino acid or dipeptide is carnosine.

In some embodiments, at least one AD diagnosis marker is an aromatic-containing free amino acid that is a neurotransmitter, such as an aromatic-containing free amino acid selected from the group consisting of tryptophan, phenylalanine, tyrosine, dopamine, and DOPA. In some embodiments, the aromatic-containing free amino acid is dopamine. In some embodiments, the aromatic-containing free amino acid is DOPA.

In some embodiments, at least one AD diagnosis marker is an imidazole-containing free amino acid or dipeptide having antioxidant properties and at least one AD diagnosis marker is an aromatic-containing free amino acid that is a neurotransmitter. In some embodiments, at least one AD diagnosis marker is a glutamate-derived free amino acid or dipeptide. In some embodiments, at least one AD diagnosis marker is an imidazole-containing free amino acid or dipeptide having antioxidant properties, at least one AD diagnosis marker is an aromatic-containing free amino acid that is a neurotransmitter, and at least one AD diagnosis marker is a glutamate-derived free amino acid or dipeptide.

In some embodiments, the AD diagnosis marker is a free amino acid or dipeptide selected from the group consisting of: histidine, 1-methyl-histidine, 3-methyl-histidine, carnosine, anserine, tryptophan, phenylalanine, tyrosine, dopamine, DOPA, arginine, citrulline, and ornithine. In some embodiments, a characteristic change of at least two (such as at least any of 3, 4, 5, 6, 7, 8, 9, 10, 11, 12, or 13) free amino acids or dipeptides selected from the group consisting of dopamine, histidine, 1-methyl-histidine, 3-methyl-histidine, carnosine, anserine, tryptophan, phenylalanine, tyrosine, DOPA, arginine, citrulline, and ornithine is indicative or suggestive of AD.

In some embodiments, the AD diagnosis marker is any of the free amino acid or dipeptide listed in Table 5. For example, in some embodiments, there is provided a method of diagnosing AD in an individual, comprising: a) comparing the CSF level of at least one AD diagnosis marker from the individual with a reference level, and b) determining whether the individual has AD based on a characteristic change in the CSF level of at least one AD diagnosis biomarker, wherein the AD diagnosis marker is selected from the group consisting of: histidine, 1-methyl histidine, 3-methyl histidine, tryptophan, phenylalanine, arginine, citrulline, pyroglutamine, 4-hydroxyproline, glycyl proline, asparagine, isoleucine, lysine, cysteine, valine, leucine, tyrosine, dopamine, glutamine, proline-hydroxyproline, proline, cystine, and glycine. In some embodiments, a decrease in the CSF level of at least one (such as at least any of 2, 3, 5, 10, 15, or more) of histidine, 1-methyl histidine, 3-methyl histidine, tryptophan, phenylalanine, arginine, citrulline, pyroglutamine, 4-hydroxyproline, glycyl proline, asparagine, isoleucine, lysine, cysteine, valine, and leucine (collectively designated as "Group 1 AD diagnosis markers") is indicative of AD. In some embodiments, an increase in the CSF level of at least one (such as at least any of 2, 3, 4, 5, 6, 7) of tyrosine, dopamine, glutamine, proline-hydroxyproline, proline, cystine, and glycine (collectively designated as "Group 2 AD diagnosis markers") is indicative of AD. In some embodiments, a decrease in the CSF level of at least one (such as at least any of 2, 3, 5, 10, 15, or more) Group 1 AD diagnosis marker and an increase in the CSF level of at least one (such as at least any of 2, 3, 4, 5, 6, 7) Group 2 AD diagnosis marker is indicative of AD.

In some embodiments, the invention provides a method of aiding diagnosis of AD in an individual, comprising: a) comparing the CSF level of at least one AD diagnosis marker from the individual with a reference level, and b) determining whether the individual has AD based on a characteristic change in the CSF level of at least one AD diagnosis biomarker and one other AD diagnosis method, wherein the AD diagnosis marker is selected from the group consisting of: histidine, 1-methyl histidine, 3-methyl histidine, tryptophan, phenylalanine, arginine, citrulline, pyroglutamine, 4-hydroxyproline, glycyl proline, asparagine, isoleucine, lysine, cysteine, valine, leucine, tyrosine, dopamine, glutamine, proline-hydroxyproline, proline, cystine, and glycine. In some embodiments, a decrease in the CSF level of at least one (such as at least any of 2, 3, 5, 10, 15, or more) of histidine, 1-methyl histidine, 3-methyl histidine, tryptophan, phenylalanine, arginine, citrulline, pyroglutamine, 4-hydroxyproline, glycyl proline, asparagine, isoleucine, lysine, cysteine, valine, and leucine ("Group 1 AD diagnosis markers") is suggestive of AD. In some embodiments, an increase in the CSF level of at least one (such as at least any of 2, 3, 4, 5, 6, 7) of tyrosine, dopamine, glutamine, proline-hydroxyproline, proline, cystine, and glycine ("Group 2 AD diagnosis markers") is suggestive of AD. In some embodiments, a decrease in the CSF level of at least one (such as at least any of 2, 3, 5, 10, 15, or more) Group 1 AD diagnosis marker and an increase in the CSF level of at least one (such as at least any of 2, 3, 4, 5, 6, 7) Group 2 AD diagnosis marker is suggestive of AD.

In some embodiments, there is provided a method of diagnosing AD in an individual, comprising: a) comparing the plasma level of at least one AD diagnosis marker from the individual with a reference level, and b) determining whether the individual has AD based on a characteristic change in the plasma level of at least one AD diagnosis biomarker, wherein the AD diagnosis marker is selected from the group consisting of: histidine, 1-methyl histidine, 3-methyl histidine, carnosine, phenylalanine, tyrosine, dopamine, arginine, citrulline, pyroglutamine, GABA, βABA, ABA, 4-hydroyproline, hydroxy lysine, lysyl alanine, aminopimelic acid, anserine, tryptophan, DOPA, ornithine, glutamic acid, γ-glutamyl-ε-lysine, DABA, glutamine, proline-hydroxyproline, glycyl proline, aspartic acid, isoleucine, lysine, serine, cysteine, cystine, cystathionine, glycine, valine, and allo-leucine. In some embodiments, a decrease in the plasma level of at least one (such as at least any of 2, 5, 10, 15, or more) of histidine, 1-methyl histidine, 3-methyl histidine, carnosine, phenylalanine, tyrosine, dopamine, arginine, citrulline, pyroglutamine, GABA, βABA, ABA, 4-hydroyproline, hydroxy lysine, lysyl alanine, aminopimelic acid (collectively designated as "Group 3 AD diagnosis markers") is indicative of AD. In some embodiments, an increase in the plasma level of at least one (such as at least any of 5, 10, 15, or 20) of anserine, tryptophan, DOPA, ornithine, glutamic acid, γ-glutamyl-ε-lysine, DABA, glutamine, proline-hydroxyproline, glycyl proline, aspartic acid, isoleucine, lysine, serine, cysteine, cystine, cystathionine, glycine, valine, and allo-leucine (collective designated as "Group 4 AD diagnosis markers) is indicative of AD. In some embodiments, a decrease in the plasma level of at least one (such as at least any of 2, 5, 10, 15, or more) Group 3 AD diagnosis marker and an increase in the plasma level of at least one (such as at least any of 5, 10, 15, or 20) Group 4 AD diagnosis marker is indicative of AD.

In some embodiments, the invention provides a method of aiding diagnosis of AD in an individual, comprising: a) comparing the plasma level of at least one AD diagnosis marker from the individual with a reference level, and b) determining whether the individual has AD based on a characteristic change in the plasma level of at least one AD diagnosis biomarker and one other AD diagnosis method, wherein the AD diagnosis marker is selected from the group consisting of: histidine, 1-methyl histidine, 3-methyl histidine, carnosine, phenylalanine, tyrosine, dopamine, arginine, citrulline, pyroglutamine, GABA, βABA, ABA, 4-hydroyproline, hydroxy lysine, lysyl alanine, aminopimelic acid, anserine, tryptophan, DOPA, ornithine, glutamic acid, γ-glutamyl-ε-lysine, DABA, glutamine, proline-hydroxyproline, glycyl proline, aspartic acid, isoleucine, lysine, serine, cysteine, cystine, cystathionine, glycine, valine, and allo-leucine. In some embodiments, a decrease in the plasma level of at least one (such as at least any of 2, 5, 10, 15, or more) of histidine, 1-methyl histidine, 3-methyl histidine, carnosine, phenylalanine, tyrosine, dopamine, arginine, citrulline, pyroglutamine, GABA, βABA, ABA, 4-hydroyproline, hydroxy lysine, lysyl alanine, aminopimelic acid ("Group 3 AD diagnosis markers") is suggestive of AD. In some embodiments, an increase in the plasma level of at least one (such as at least any of 5, 10, 15, or 20) of anserine, tryptophan, DOPA, ornithine, glutamic acid, γ-glutamyl-ε-lysine, DABA, glutamine, proline-hydroxyproline, glycyl proline, aspartic acid, isoleucine, lysine, serine, cysteine, cystine, cystathionine, glycine, valine, and allo-leucine ("Group 4 AD diagnosis markers) is suggestive of AD. In some embodiments, a decrease in the plasma level of at least one (such as at least any of 2, 5, 10, 15, or more) Group 3 AD diagnosis marker and an increase in the plasma level of at least one (such as at least any of 5, 10, 15, or 20) Group 4 AD diagnosis marker is suggestive of AD.

In some embodiments, there is provided a method of diagnosing AD in an individual, comprising: a) comparing the urine level of at least one AD diagnosis marker from the individual with a reference level, and b) determining whether the individual has AD based on a characteristic change in the urine level of at least one AD diagnosis biomarker, wherein the AD diagnosis marker is selected from the group consisting of: 1-methyl-histindine, anserine, pyroglutamine, DABA, threonine, lysine, cystathionine, valine, histidine, 3-methyl histidine, carnosine, tryptophan, phenylalanine, tyrosine, arginine, citrulline, ornithine, glutamine, proline-hydroproline, 4-hydroxyproline, glycyl proline, asparagine, isoleucine, lysyl alanine, cysteine, cystine, glycine, and leucine. In some embodiments, a decrease in the urine level of at least one (such as at least any of 2, 3, 4, 5, 6, 7, or 8) of 1-methyl-histindine, anserine, pyroglutamine, DABA, threonine, lysine, cystathionine, valine (collectively designated as "Group 5 AD diagnosis markers") is indicative of AD. In some embodiments, an increase in urine level of at least one (such as at least any of 5, 10, 15, or 20) of histidine, 3-methyl histidine, carnosine, tryptophan, phenylalanine, tyrosine, arginine, citrulline, ornithine, glutamine, proline-hydroproline, 4-hydroxyproline, glycyl proline, asparagine, isoleucine, lysyl alanine, cysteine, cystine, glycine, and leucine (collectively designated as "Group 6 AD diagnosis markers") is indicative of AD. In some embodiments, a decrease in urine level of at least one (such as at least any of 2, 3, 4, 5, 6, 7, or 8) Group 5 AD diagnosis marker and an increase in urine level of at least one (such as at least any of 5, 10, 15, or 20) Group 6 AD diagnosis marker is indicative of AD.

In some embodiments, the invention provides a method of aiding diagnosis of AD in an individual, comprising: a) comparing the urine level of at least one AD diagnosis marker from the individual with a reference level, and b) determining whether the individual has AD based on a characteristic change in the urine level of at least one AD diagnosis biomarker and one other AD diagnosis method, wherein the AD diagnosis marker is selected from the group consisting of: 1-methyl-histindine, anserine, pyroglutamine, DABA, threonine, lysine, cystathionine, valine, histidine, 3-methyl histidine, carnosine, tryptophan, phenylalanine, tyrosine, arginine, citrulline, ornithine, glutamine, proline-hydroproline, 4-hydroxyproline, glycyl proline, asparagine, isoleucine, lysyl alanine, cysteine, cystine, glycine, and leucine. In some embodiments, a decrease in the urine level of at least one (such as at least any of 2, 3, 4, 5, 6, 7, or 8) of 1-methyl-histindine, anserine, pyroglutamine, DABA, threonine, lysine, cystathionine, valine (collectively designated as "Group 5 AD diagnosis markers") is suggestive of AD. In some embodiments, an increase in urine level of at least one (such as at least any of 5, 10, 15, or 20) of histidine, 3-methyl histidine, carnosine, tryptophan, phenylalanine, tyrosine, arginine, citrulline, ornithine, glutamine, proline-hydroproline, 4-hydroxyproline, glycyl proline, asparagine, isoleucine, lysyl alanine, cysteine, cystine, glycine, and leucine (collectively designated as "Group 6 AD diagnosis markers") is suggestive of AD. In some embodiments, a decrease in urine level of at least one (such as at least any of 2, 3, 4, 5, 6, 7, or 8) Group 5 AD diagnosis marker and an increase in urine level of at least one (such as at least any of 5, 10, 15, or 20) Group 6 AD diagnosis marker is suggestive of AD.

In some embodiments, the levels of AD diagnosis markers in more than one body fluid is determined. For example, in some embodiments, the plasma level of at least one Group 3 or Group 4 AD diagnosis markers and the urine level of at least one Group 5 or Group 6 AD diagnosis markers are determined, and diagnosis of AD can be based on a characteristic change of one or more of these AD diagnosis markers.

The methods described herein are also useful for any one or more of: diagnosing and aiding diagnosis of mild cognitive impairment ("MCI"), diagnosing and aiding diagnosis of mild cognitive deficit, assessing cognitive function, assessing cognitive impairment, predicting risk of developing AD, monitoring AD progression of AD, monitoring AD treatment, and screening for individuals having AD.

In another aspect, there are provided methods of diagnosing and treating AD based on the plasma level of carnosine or the enzymatic activities of the carnosine synthesis pathway in the plasma. In some embodiments, the method comprises: a) comparing the plasma level of carnosine of the individual with a reference level, and b) determining whether the individual has AD based on a decrease in the plasma level of carnosine. For example, in some embodiments, a decrease in the plasma level of carnosine by at least about 40% is indicative of AD. In some embodiments, the method comprises: a) comparing the relative activity of carnosinase versus carnosine synthetase in the plasma of the individual with a reference relative activity, and b) determining whether the individual has AD based on an increase in the relative activity. In some embodiments, the method comprises: a) comparing the activity of carnosine synthetase in the plasma of the individual with a reference activity, and b) determining whether the individual has AD based on a decrease in the activity of carnosine synthetase. In some embodiments, the method comprises: a) comparing the activity of carnosinase or carnosine-N-methyltransferase in the plasma of the individual with a reference activity, and b) determining whether the individual has AD based on an increase in the activity of carnosinase or carnosine-N-methyltransferase.

In some embodiments, there is provided a method of treating AD in an individual, comprising administering to the individual an effective amount of an agent that increases the plasma level of carnosine, wherein diagnosis of AD is based on a decrease in the plasma level of carnosine in the individual as compared to a reference level. In some embodiments, there is provided a method of treating AD in an individual, comprising: a) determining whether the individual has AD based on a decrease in the plasma level of carnosine in the individual as compared to a reference level, and b) administering to the individual an effective amount of an agent that increases the plasma level of carnosine. Methods of monitoring effectiveness of AD treatment and continuing to treat AD based on plasma level of carnosine are also provided. Agents that increase the plasma level of carnosine include, for example, carnosine itself, agents that inhibit the activity of carnosinase, and agents that enhance the activity of carnosine synthetase in the plasma.

In another aspect, there are provided methods of diagnosing and treating Alzheimer's disease ("AD") based on the plasma level of dopamine or DOPA or the enzymatic activities in the dopamine synthesis pathway. For example, in some embodiments, there is provided a method of diagnosing Alzheimer's disease ("AD") in an individual, comprising: a) comparing the plasma level of dopamine of the individual with a reference level, and b) determining whether the individual has AD based on a decrease in the plasma level of dopamine and an increase in the plasma level of DOPA. In some embodiments, a decrease in the plasma level of dopamine by at least about 15% is indicative of AD. In some embodiments, an increase in the plasma level of DOPA by at least about 50% is indicative of AD. In some embodiments, an increase in the plasma level of DOPA and decrease in the plasma level of dopamine is indicative of AD. In some embodiments, an increase in the plasma level of DOPA by at least about 50% and a decrease in the plasma level of dopamine by at least about 15% is indicative of AD.

In some embodiments, there is provided a method of diagnosing AD in an individual, comprising: a) comparing the relative activity of tyrosine-3-hydrolase versus DOPA decarboxylase in the plasma of the individual with a reference relative activity, and b) determining whether the individual has AD based on an increase in the relative activity. In some embodiments, there is provided a method of diagnosing AD in an individual, comprising: a) comparing the activity of DOPA decarboxylase in the plasma of the individual with a reference activity, and b) determining whether the individual has AD based on a decrease in the activity of DOPA decarboxylase. In some embodiments, there is provided a method of diagnosing AD in an individual, comprising: a) comparing the activity of tyrosine-3-hydrolase in the plasma of the individual with a reference activity, and b) determining whether the individual has AD based on an increase in the activity of tyrosine-3-hydrolase.

In some embodiments, there is provided a method of treating AD in an individual, comprising administering to the individual an effective amount of an agent that increases the plasma level of dopamine or decreases the plasma level of DOPA, wherein diagnosis of AD is based on a decrease in the plasma level of dopamine or an increase in the plasma level of DOPA in the individual as compared to a reference level. In some embodiments, there is provided a method of treating AD in an individual, comprising: a) determining whether the individual has AD based on a decrease in the plasma level of dopamine or an increase in the plasma level of DOPA in the individual as compared to a reference level, and b) administering to the individual an effective amount of an agent that increases the plasma level of dopamine or decreases the plasma level of DOPA. Methods of monitoring effectiveness of AD treatment and methods of continuing to treat AD based on plasma level of carnosine are also provided. Agents that increase the plasma level of dopamine or decrease the plasma level of DOPA include, for example, dopamine itself, agents that inhibit tyrosine-3-hydrolase, and agents that enhance DOPA dehydroxylase in the plasma.

In another aspect, there are provided methods of simultaneously determining the levels of at least two free amino acids or dipeptides in a biological fluid sample using liquid chromatography tandem mass spectrometry ($LCMS^2$ method). For example, in some embodiments, there is provided a method of simultaneously measuring the levels of at least two (such as at least any of 3, 5, 10, 15, 20, 30, 40, 50, 60, 70, 80, or more) free amino acids or dipeptides in a biological fluid sample, comprising subjecting the sample to $LCMS^2$, wherein the levels of at least two (such as at least any of 3, 5, 10, 15, 20, 30, 40, 50, 60, 70, 80, or more) free amino acids or dipeptides are determined.

In some embodiments, there is provided a method of assessing changes in levels of at least one free amino acids or dipeptides in a biological fluid sample, comprising simultaneously detecting levels of at least two (such as at least any of 2, 3, 5, 10, 20, 30, 40, 50, 60, 70, 80, or more) free amino acids or dipeptides in the sample by $LCMS^2$ and comparing the detected levels with reference levels. In some embodiments, a characteristic change in at least one of the free amino acids or dipeptides are indicative of a disease, such as AD.

In some embodiments, there is provided a method of identifying one or more diagnosis markers of a disease, comprising simultaneously measuring the levels of at least two free amino acids or dipeptides from a set of biological fluid samples by LCMS², wherein the set of biological fluid samples is divisible into subsets on the basis of a disease, comparing the levels from each subset for at least one biomarker, and identifying at least one marker for which the levels are significantly different between the two subsets. In some embodiments, the method comprises simultaneously measuring the levels of at least 2, 3, 5, 10, 20, 30, 40, 50, 60, 70, 80, or more free amino acids or dipeptides. In some embodiments, the disease is AD.

BRIEF DESCRIPTION OF THE FIGURES

FIG. 1A provides the TIC (Total Ion Current) of free amino acid and dipeptide standards. FIGS. 1B-1F provides the extracted SRM chromatograph of five internal standards. FIG. 1G provides the standard curve for L-DOPA using [$^2H_4$]-DOPA as an internal standard.

FIG. 2A provides the TIC of amino acids and dipeptides in CSF obtained by LCMS in the SRM mode. FIGS. 2B-2F provide spectra of homophenylalanine internal standard (B), citrulline (C), carnosine (D), phenylalanine (E), and L-DOPA (F). The arrows indicate peaks corresponding to the retention times of authentic free amino acid standards.

FIG. 3A provides TIC of amino acids and dipeptides in plasma obtained by LCMS² in the SRM mode. FIGS. 3A-3F provide spectra of homophenylalanine internal standard (B), citrulline (C), carnosine (D), phenylalanine (E), and L-DOPA (F). The arrows indicate peaks corresponding to the retention times of authentic free amino acid standards.

FIG. 4A provides TIC of amino acids and dipeptides in urine obtained by LCMS² in the SRM mode. FIGS. 4A-4F provide spectra of homophenylalanine internal standard (B), citrulline (C), carnosine (D), phenylalanine (E), and L-DOPA (F). The arrows indicate peaks corresponding to the retention times of authentic free amino acid standards.

DETAILED DESCRIPTION OF THE INVENTION

Figure 5:
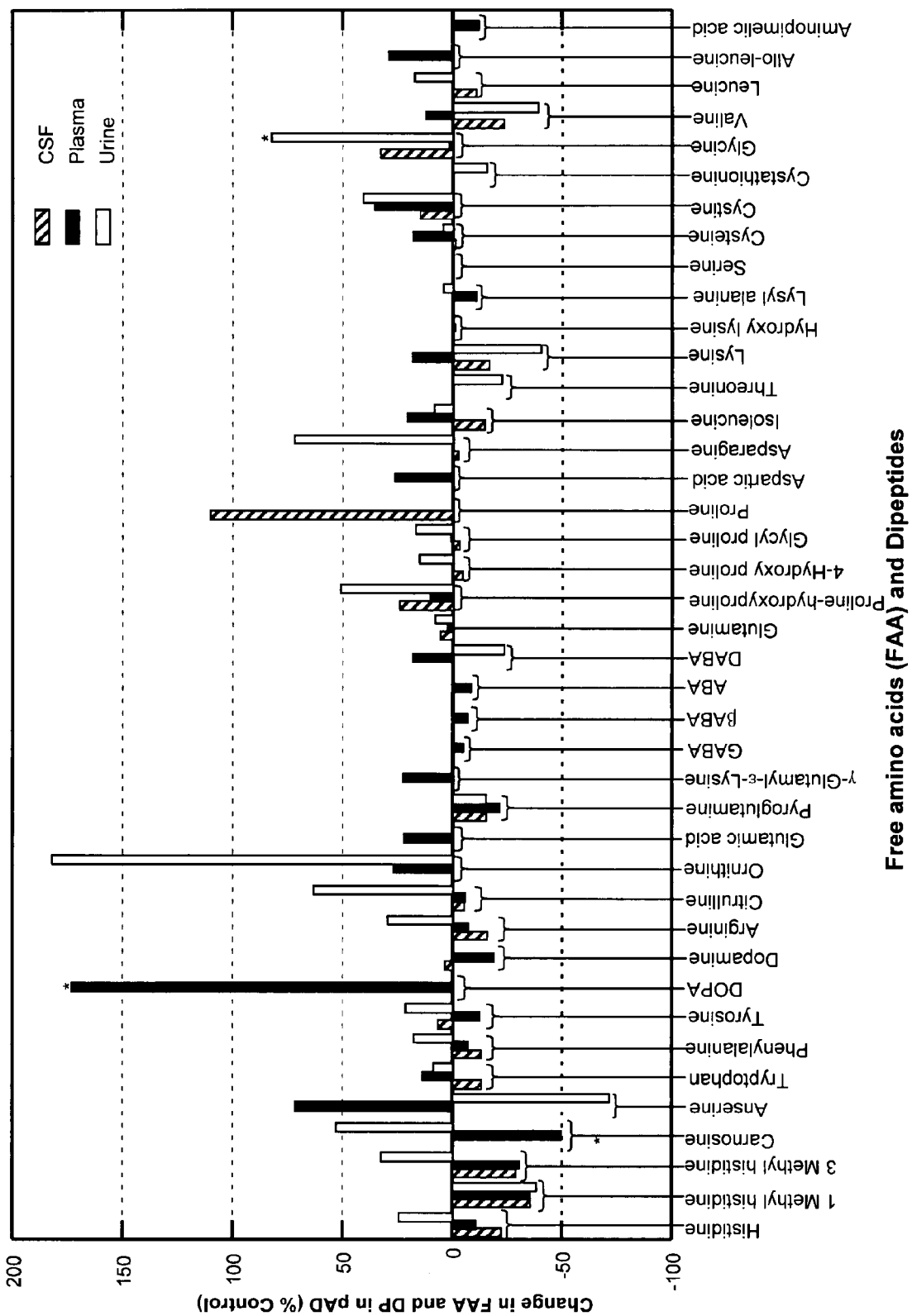
FIG. 5 provides a diagram showing changes of free amino acids and dipeptide concentrations in samples from AD patients. Changes are represented as the percentage change in samples from AD patients as compared to normal individuals (*, p<0.05). Changes are determined based on the mean concentration of free amino acids and dipeptides in AD patients (n=8) and control individuals (n=8).

We have developed a sensitive and specific liquid chromatography tandem mass spectrometry method ("LCMS²") for simultaneous determination of levels of multiple free amino acids and dipeptides in a biologic fluid sample. Using this method, we have identified a collection of free amino acids or dipeptides whose levels are altered in Alzheimer's disease patients as compared to those of normal individuals. These free amino acids or dipeptides (collective termed "AD diagnosis markers") can be used, either individually or in various combinations, to diagnose AD or aid diagnosis of AD. By analyzing these AD diagnosis markers, we have also identified the carnosine synthesis pathway and the dopamine synthesis pathway as central biochemical pathways underlying the AD pathology. We propose that the activities of these metabolic pathways may be useful for diagnosis of AD and that manipulation of such may be useful for treating AD.

Accordingly, the invention in one aspect provides methods of diagnosing AD or aiding diagnosis of AD based on the levels of AD diagnosis markers.

In another aspect, there are provided methods of diagnosing AD based on carnosine level and/or carnosine synthesis activities in the plasma. Methods of treatment with agents that increase plasma carnosine level are also provided.

In another aspect, there are provided methods of diagnosing AD based on dopamine/DOPA level and/or dopamine synthesis activities in the plasma. Methods of treatment with agents that increase plasma dopamine level and/or decrease DOPA level are also provided.

In another aspect, there are provided methods of simultaneously determining the levels of two or more free amino acids or dipeptides in a biological fluid sample. These methods are useful for assessing changes in free amino acids or dipeptides in a biological fluid sample, identifying disease markers (for example for the purpose of diagnosing disease), and elucidating biochemical pathways underlying diseases.

As used herein, "a", "an", and "the" can mean singular or plural (i.e., can mean one or more) unless indicated otherwise.

Methods of Diagnosing AD Based on AD Diagnosis Markers

The present invention in one aspect provides a method of diagnosing Alzheimer's disease ("AD") in an individual, comprising: a) comparing the level of at least one AD diagnosis marker in a body fluid sample from the individual (such as an individual suspected of having or being susceptible to AD) with a reference level, and b) determining whether the individual has AD based on a characteristic change in the level of at least one AD diagnosis biomarker. In some embodiments, the AD diagnosis marker is a free amino acid or dipeptide selected from the group consisting of: an imidazole-containing free amino acid or dipeptide having antioxidant properties, an aromatic-containing free amino acid that is a neurotransmitter, a free amino acid or dipeptide associated with urea metabolism or detoxification and NO formation, a glutamate-derived free amino acid or dipeptide, and an asparate or serine-derived free amino acid. In some embodiments, the AD diagnosis marker is a free amino acid or dipeptide selected from the group consisting of histidine, 1-methyl-histidine, 3-methyl-histidine, carnosine, anserine, tryptophan, phenylalanine, tyrosine, dopamine, DOPA, arginine, citrulline, and ornithine. In some embodiments, the AD diagnosis marker is a free amino acid or dipeptide listed in Table 5. In some embodiments, the AD diagnosis markers are present in peripheral body fluids (e.g., plasma and urine) of individuals, allowing simple and non-invasive diagnosis of AD.

In some embodiments, the method comprises: a) providing a body fluid sample from the individual (such as an individual suspected of having or being susceptible to AD), b) comparing the level of at least one AD diagnosis marker in a body fluid sample from the individual with a reference level, and c) determining whether the individual has AD based on a characteristic change in the level of at least one AD diagnosis biomarker. In some embodiments, there is provided a method of diagnosing AD in an individual, comprising: a) determining the level of at least one AD diagnosis marker in the body fluid sample of the individual (such as an individual suspected of having or being susceptible to AD), b) comparing the level of at least one AD diagnosis marker in a body fluid sample with a reference level, and c) determining whether the individual has AD based on a characteristic change in the level of at least one AD diagnosis biomarker. In some embodiments, there is provided a method of diagnosing AD in an individual, comprising: a) providing a body fluid sample from the individual, b) determining the level of at least one AD diagnosis marker in the body fluid sample, c) comparing the level of at least one AD diagnosis marker in a body fluid sample with a reference level, and d) determining whether the individual has AD based on a characteristic change in the level of at least one AD diagnosis biomarker.

The present invention also encompasses methods of providing information about the levels of AD diagnosis markers in an individual (such as an individual suspected of having or being susceptible to AD). Such information (either quantitative or qualitative) can then be used for diagnosis of AD. For example, in some embodiments, there is provided a method comprising: a) determining the level of at least one AD diagnosis marker in the body fluid sample of the individual (such as an individual suspected of having or being susceptible to AD), and b) providing information about the level of at least one AD diagnosis marker for diagnosis of AD, wherein the level of the at least one AD diagnosis marker is used as basis for diagnosing AD, and wherein a characteristic change in the level of the at least one AD diagnosis biomarker is indicative of AD. Also provided are methods of evaluating results of the analytical methods described herein. Such evaluation generally entails reviewing the result(s) and can assist, for example, in advising regarding clinical and/or diagnostic follow-up and/or treatment options.

The AD diagnosis markers described herein are also useful for aiding diagnosis of AD. As used herein, methods for "aiding diagnosis" refer to methods that assist in making a clinical determination regarding the presence or nature of the AD, and may or may not be conclusive with respect to the definitive diagnosis. For example, the methods described herein may be used in conjunction with other methods for diagnosing AD. Other methods of diagnosing AD are known in the art, and include, for example, ADAS-COG, MMSE, magnetic resonance imaging, magnetic resonance spectrometry, and measurement of β-amyloid and tau levels. Accordingly, in some embodiments, there is provided a method of aiding diagnosis of AD, comprising: a) comparing the level of at least one AD diagnosis marker in a body fluid sample from the individual with a reference level, and b) determining whether the individual has AD based on a characteristic change in the level of at least one AD diagnosis biomarker and at least one other method of diagnosing AD. In some embodiments, the other method is a cognition test. In some embodiments, the other method is a behavior test. In some embodiments, the method comprises: a) providing a body fluid sample from the individual (such as an individual suspected of having or being susceptible to AD), b) comparing the level of at least one AD diagnosis marker in a body fluid sample from the individual with a reference level, and c) determining whether the individual has AD based on a characteristic change in the level of at least one AD diagnosis biomarker and at least one other method of diagnosing AD. In some embodiments, there is provided a method of aiding diagnosis of AD in an individual, comprising: a) determining the level of at least one AD diagnosis marker in the body fluid sample of the individual (such as an individual suspected of having or being susceptible to AD), b) comparing the level of at least one AD diagnosis marker in a body fluid sample with a reference level, and c) determining whether the individual has AD based on a characteristic change in the level of at least one AD diagnosis biomarker and at least one other method of diagnosing AD. In some embodiments, there is provided a method of aiding diagnosis of AD in an individual, comprising: a) providing a body fluid sample from the individual, b) determining the level of at least one AD diagnosis marker in the body fluid sample, and c) comparing the level of at least one AD diagnosis marker in a body fluid sample with a reference level, and d) determining whether the individual has AD based on a characteristic change in the level of at least one AD diagnosis biomarker and at least one other method of diagnosing AD. In some embodiments, there is provided a method of aiding diagnosis of AD, comprising: a) determining the level of at least one AD diagnosis marker in the body fluid sample of the individual, and b) providing information about the level of at least one AD diagnosis marker for diagnosis of AD, wherein the level of the at least one AD diagnosis marker is used as basis for aiding diagnosis of AD, and wherein a characteristic change in the level of at least one AD diagnosis marker is suggestive of AD.

In some embodiments, there is provided a method of diagnosing or aiding diagnosis of mild cognitive impairment ("MCI"). In some embodiments, the invention provides a method of diagnosing MCI in an individual, comprising: a) comparing the level of at least one AD diagnosis marker in a body fluid sample from the individual (such as an individual suspected of having or being susceptible to MCI) with a reference level, and b) determining whether the individual has MCI based on a characteristic change in the level of at least one AD diagnosis biomarker. In some embodiments, there is provided a method comprising: a) determining the level of at least one AD diagnosis marker in the body fluid sample of the individual (such as an individual suspected of having or being susceptible to MCI), and b) providing information about the level of at least one AD diagnosis marker for diagnosis of MCI, wherein the level of the at least one AD diagnosis marker is used as basis for diagnosing MCI, and wherein a characteristic change in the level of the at least one AD diagnosis biomarker is indicative of MCI. In some embodiments, there is provided a method of aiding diagnosis of MCI, comprising: a) comparing the level of at least one AD diagnosis marker in a body fluid sample from the individual with a reference level, and b) determining whether the individual has MCI based on a characteristic change in the level of at least one AD diagnosis biomarker and at least one other method of diagnosing MCI. In some embodiments, the other method is a cognition test. Other methods for diagnosing MCI include, for example, neurocognitive testing such as the Wechsler adult intelligence testing and neuroimaging such as measurements of the hippocampal volume. In some embodiments, there is provided a method of aiding diagnosis of MCI, comprising: a) determining the level of at least one AD diagnosis marker in the body fluid sample of the individual, and b) providing information about the level of at least one AD diagnosis marker for diagnosis of MCI, wherein the level of the at least one AD diagnosis marker is used as basis for aiding diagnosis of MCI, and wherein a characteristic change in the level of at least one AD diagnosis marker is suggestive of MCI.

In some embodiments, there is provided a method of stratifying AD patients. As used herein, the term "stratifying" refers to sorting individuals into different classes or strata based on the features of a neurological disease. For example, stratifying a population of individual with AD may involve assigning the individual on the basis of the severity of the disease (e.g., mild, moderate, advanced, etc.). Stratifying a population of individual with AD may also involve assigning the individual on the basis of progression rate of AD (e.g., slow, fast, etc.).

In some embodiments, there is provided a method of predicting whether the individual is at risk of developing AD. As used herein, the term "predicting" refers to making a finding that an individual has a significantly enhanced probability of developing an AD.

The AD diagnosis markers described herein are also useful for one or more of the following: monitoring AD progression in AD patients, monitoring AD treatment in AD patients, screening for individuals having AD, assessing cognitive function, assessing cognitive impairment, and diagnosing or aiding diagnosis of cognitive impairment, based on the levels of one or more AD diagnosis levels in a body fluid sample.

An "individual" as used herein refers to a vertebrate, preferably a mammal, more preferably a human. Mammals include, but are not limited to, farm animals, sport animals, pets, primates, mice and rats. In some embodiments, the individual is human. In some embodiments, the individual is an individual other than human. In some embodiments, the individual is an animal model for the study of AD. Animal models for AD studies are known in the art. See, for example, Haltzman et al., Proc. Natl. Acad. Sci. USA, 2000, 97(6): 2892-7.

In some embodiments, the individual is a normal individual, e.g., an individual having a Mini-Mental State Examination (MMSE) score or would achieve a MMSE score in the range of 25-30. In some embodiments, the individual is an individual with mild AD, e.g., an individual who has either been assessed with the Mini-Mental State Examination (MMSE) and scored 22-27 or would achieve a score of 22-27 upon MMSE testing. In some embodiments, the individual is an individual with moderate AD, e.g., an individual who has either been assessed with the MMSE and scored 16-21 or would achieve a score of 16-21 upon MMSE testing. In some embodiments, the individual is an individual with severe AD, e.g., an individual who has either been assessed with the MMSE and scored 12-15 or would achieve a score of 12-15 upon MMSE testing.

In some embodiments, the individual is suspected of having AD or MCI. In some embodiments, the individual is an individual for whom cognitive assessment is desired. Alternatively, an individual involved in for example research and/or clinical research may desire an assessment without any indication of AD, suspected AD, or at risk of AD. In some embodiments, the individual is 65 years or older. In some embodiments, the individual is a man. In some embodiments, the individual is a woman.

A "biological fluid sample" described herein encompasses a variety of fluid sample types obtained from an individual and can be used in a diagnostic or monitoring assay. The definition encompasses body fluid (such as plasma, cerebral spinal fluid (CSF), urine). The biological fluid sample (such as a body fluid sample) may have been manipulated in any way after their procurement, such as by treatment with reagents, solubilization, or enrichment for certain components, such as proteins or polynucleotides.

AD Diagnosis Markers

"AD diagnosis markers" is used herein as a term of convenience to refer to the markers described herein and their use, and is not intended to indicate that the markers are only used to diagnose AD. As this disclosure makes clear, these markers are useful for, for example, diagnosing and aiding diagnosis of MCI, assessing cognitive function, and assessing risk of developing AD.

In some embodiments, the AD diagnosis marker is a free amino acid or dipeptide selected from the group consisting of: an imidazole-containing free amino acid or dipeptide having antioxidant properties, an aromatic-containing free amino acid that is a neurotransmitter, a free amino acid or dipeptide associated with urea metabolism or detoxification and NO formation, a glutamate-derived free amino acid or dipeptide, and an asparate or serine-derived free amino acid. In some embodiments, the AD diagnosis marker is a free amino acid or dipeptide selected from the group consisting of histidine, 1-methyl-histidine, 3-methyl-histidine, carnosine, anserine, tryptophan, phenylalanine, tyrosine, dopamine, DOPA, arginine, citrulline, and ornithine. In some embodiments, the AD diagnosis marker is a free amino acid or dipeptide listed in Table 5.

Imidazole-containing free amino acids or dipeptides having antioxidant properties include, for example, histidine, 1-methyl-histidine, 3-methyl-histidine, carnosine, and anserine.

Aromatic-containing free amino acids that are neurotransmitters include, for example, tryptophan, phenylalanine, tyrosine, DOPA, and dopamine.

Free amino acids or dipeptides associated with urea metabolism or detoxification and NO formation include, for example, arginine, citrulline, and ornithine.

Glutamate-derived free amino acids or dipeptides include, for example, glutamic acid, pyroglutamine, γ-glutamyl-ε-lysine, GABA, βABA, ABA, DABA, and glutamine.

Asparate or serine-derived free amino acids include, for example, aspartic acid, asparagine, isoleucine, threonine, lysyl alanine, lysine, hydroxy lysine, serine, cystathionine, cystine, and cysteine.

The AD diagnosis marker may also be a proline containing free amino acid or dipeptide, including, for example, proline-hydroxyproline, 4-hydroxyproline, glycylproline, and proline. In some embodiments, the AD diagnosis marker is glycine, valine, leucine, allo-leucine, and aminopimelic acid.

In some embodiments, the AD diagnosis marker is a free amino acid or dipeptide selected from the groups consisting of histidine, 1-methyl histidine, 3-methyl histidine, tryptophan, phenylalanine, arginine, citrulline, pyroglutamine, 4-hydroxyproline, glycyl proline, asparagine, isoleucine, lysine, cysteine, valine, and leucine. The CSF levels of these free amino acids or dipeptides (collectively designated as "Group 1 AD diagnosis markers") decrease in individuals having AD as compared to reference levels.

In some embodiments, the AD diagnosis marker is a free amino acid or dipeptide selected from the group consisting of tyrosine, dopamine, glutamine, proline-hydroxyproline, proline, cystine, and glycine. The CSF levels of these free amino acids and dipeptides (collectively designated as 'Group 2 AD diagnosis markers") increase in individuals having AD as compared to reference levels.

In some embodiments, the AD diagnosis marker is a free amino acid or dipeptide selected from the group consisting of histidine, 1-methyl histidine, 3-methyl histidine, carnosine, phenylalanine, tyrosine, dopamine, arginine, citrulline, pyroglutamine, GABA, βABA, ABA, 4-hydroyproline, hydroxy lysine, lysyl alanine, aminopimelic acid. The plasma levels of these free amino acids or dipeptides (collectively designated as "Group 3 AD diagnosis markers") decrease in individuals having AD as compared to reference levels.

In some embodiments, the AD diagnosis marker is a free amino acid or dipeptide selected from the group consisting of anserine, tryptophan, DOPA, ornithine, glutamic acid, γ-glutamyl-ε-lysine, DABA, glutamine, proline-hydroxyproline, glycyl proline, aspartic acid, isoleucine, lysine, serine, cysteine, cystine, cystathionine, glycine, valine, and allo-leucine. The plasma levels of these free amino acids or dipeptides (collective designated as "Group 4 AD diagnosis markers) increase in individuals having AD as compared to reference levels.

In some embodiments, the AD diagnosis marker is a free amino acid or dipeptide selected from the group consisting of 1-methyl-histindine, anserine, pyroglutamine, DABA, threonine, lysine, cystathionine, and valine. The urine levels of these free amino acids or dipeptides (collectively designated as "Group 5 AD diagnosis markers") decrease in individuals with AD as compared to reference levels.

In some embodiments, the AD diagnosis marker is a free amino acid or dipeptide selected from the group consisting of histidine, 3-methyl histidine, carnosine, tryptophan, phenylalanine, tyrosine, arginine, citrulline, ornithine, glutamine, proline-hydroproline, 4-hydroxyproline, glycyl proline, asparagine, isoleucine, lysyl alanine, cysteine, cystine, glycine, and leucine. The urine levels of these free amino acids or dipeptides (collectively designated as "Group 6 AD diagnosis markers") increase in individuals with AD as compared to reference levels.

Although acceptable levels of sensitivity and specificity with a single AD diagnosis marker can be achieved for practice of the methods described herein, the effectiveness (e.g., sensitivity and/or specificity) of the methods described herein are generally enhanced when at least two AD diagnosis markers are utilized. In some embodiments, at least 3, 4, 5, 6, 7, 8, 9, 10, 15, 20, 25, 30, or more AD diagnosis markers are utilized.

In some embodiments, the levels of at least two of imidazole-containing free amino acids or dipeptides having antioxidant properties in a body fluid (such as CSF, plasma, and urine) are determined. In some embodiments, the levels of at least two of aromatic-containing free amino acids that are neurotransmitters in a body fluid (such as CSF, plasma, and urine) are determined. In some embodiments, the levels of at least two free amino acids or dipeptides associated with urea metabolism or detoxification and NO formation in a body fluid (such as CSF, plasma, and urine) are determined. In some embodiments, the levels of at least two glutamate-derived free amino acids or dipeptides in a body fluid (such as CSF, plasma, and urine) are determined. In some embodiments, the levels of at least two aspirate or serine-derived free amino acids in a body fluid (such as CSF, plasma, and urine) are determined.

In some embodiments, the CSF levels of at least two (such as at least any of 3, 4, 5, 10, 15, or more) of Group 1 AD diagnosis markers are determined. In some embodiments, the CSF levels of at least two (such as at least any of 3, 4, 5, 6, or 7) of Group 2 AD diagnosis markers are determined. In some embodiments, the plasma levels of at least two (such as at least any of 3, 5, 10, 15, or more) of Group 3 AD diagnosis markers are determined. In some embodiments, the plasma levels of at least two (such as at least any of 5, 10, 15, or 20) of Group 4 AD diagnosis markers are determined. In some embodiments, the urine levels of at least two (such as at least any of 3, 4, 5, 6, 7, or 8) of Group 5 AD diagnosis markers are determined. In some embodiments, the urine levels of at least two (such as at least any of 3, 5, 10, 15, 20, or more) of Group 6 AD diagnosis markers are determined.

In some embodiments, the AD diagnosis markers may be partially diverse, i.e., the AD diagnosis markers may represent at least two different clusters. For example, in some embodiments, one set of AD diagnosis markers are imidazole-containing free amino acids or dipeptides having antioxidant properties, and one set of AD diagnosis markers are aromatic-containing free amino acids that are neurotransmitters.

Exemplary combinations of AD diagnosis markers include, for example, an imidazole-containing free amino acid or dipeptide having antioxidant properties combined with one or more of: an aromatic-containing free amino acid that is a neurotransmitter, a free amino acid or dipeptide associated with urea metabolism or detoxification and NO formation, a glutamate-derived free amino acid or dipeptide, and an asparate or serine-derived free amino acid; an aromatic-containing free amino acid that is a neurotransmitter combined with one or more of: an imidazole-containing free amino acid or dipeptide having antioxidant properties, a free amino acid or dipeptide associated with urea metabolism or detoxification and NO formation, a glutamate-derived free amino acid or dipeptide, and an asparate or serine-derived free amino acid; a glutamate-derived free amino acid or dipeptide combined with one or more of: an imidazole-containing free amino acid or dipeptide having antioxidant properties, an aromatic-containing free amino acid that is a neurotransmitter, a free amino acid or dipeptide associated with urea metabolism or detoxification and NO formation, and an asparate or serine-derived free amino acid. In some embodiments, at least one of the AD diagnosis markers is an imidazole-containing free amino acid or dipeptide having antioxidant properties and at least one of the AD diagnosis markers is an aromatic-containing free amino acid that is a neurotransmitter. In some embodiments, at least one of the AD diagnosis markers is an imidazole-containing free amino acid or dipeptide having antioxidant properties, at least one of the AD diagnosis markers is an aromatic-containing free amino acid that is a neurotransmitter, and at least one of the AD diagnosis markers is a glutamate-derived free amino acid or dipeptide.

Combinations of various groups of AD diagnosis markers are also contemplated. Exemplary combinations of AD diagnosis markers include: Group 1 AD diagnosis marker(s) combined with one or more of any of Group 2, 3, 4, 5, or 6 AD diagnosis markers; Group 2 AD diagnosis marker(s) combined with one or more of any of Group 1, 3, 4, 5, or 6 AD diagnosis markers; Group 3 AD diagnosis marker(s) combined with one or more Groups 1, 2, 4, 5, or 6 AD diagnosis markers; Group 4 AD diagnosis marker(s) combined with one or more of any of Group 1, 2, 3, 5, or 6 AD diagnosis markers; Group 5 diagnosis marker(s) combined with one or more of any of Group 1, 2, 3, 4, or 6 AD diagnosis markers; Group 6 AD diagnosis marker(s) combined with any of Group 1, 2, 3, 4, or 5 AD diagnosis markers. For example, in some embodiments, the CSF levels of at least one Group 1 AD diagnosis marker and at least one Group 2 AD diagnosis marker are determined. In some embodiments, the plasma levels of at least one Group 3 AD diagnosis marker and at least one Group 4 AD diagnosis marker are determined. In some embodiments, the urine levels of at least one Group 5 AD diagnosis marker and at least one Group 6 AD diagnosis markers are determined. In some embodiments, the plasma level of at least one Group 3 or Group 4 AD diagnosis marker and the urine level of at least one Group 5 or Group 6 AD diagnosis markers are determined. Other combinations are also contemplated.

Determining and Comparing Levels of AD Diagnosis Markers

Methods of determining levels of AD diagnosis markers are known in the art. For example, HPLC with derivatized samples, low capacity cation-exchange HPLC, TLC, microfluidic devices, NMR, immunoassays, and capillary electrophoresis can all be used. Methods for determining levels of free amino acids and/or dipeptides can be found, for example, in Durkin et al., 1988, *J. Chromatogr.* 428, 9-15; Husek, 1991, *FEBS Lett.* 280, 354-356; Petritis et al., 2000, *J. Chromatogr. A* 896, 253-263; Piraud et al., 2005, *Rapid Commun. Mass Spectrom.* 19, 3287-3297; Schwarz et al., 2005, *Clin. Chim. Acta* 354, 83-90; and Cellar et al., 2005, *Anal. Chem.* 77, 7067-7073. In some embodiments, the levels of the AD diagnosis markers are determined using liquid chromatography mass spectrometry, such as the $LCMS^2$ method described further below.

In certain embodiments, levels of the AD diagnosis markers are obtained from an individual at more than one time point. Such "serial" sampling is well suited for the aspects of the invention relating to monitoring progression of AD in an individual having AD. Serial sampling can be performed on any desired timeline, such as monthly, quarterly, semi-annually, annually, biennially, or less frequently. The comparison between the measured levels and the reference level may be carried out each time a new sample is measured, or the data relating to levels may be held for less frequent analysis.

For methods described herein, the reference level is generally a predetermined level that is considered "normal" for the particular AD diagnosis marker (e.g., an average level for age-matched or gender-matched individuals not diagnosed with AD). In some embodiments, the reference level is determined contemporaneously (e.g., a reference level that is derived from a pool of samples including the sample being tested).

The reference levels used for comparison may vary among the various aspects of the invention being practiced. For example, for AD diagnosis methods, the "reference level" is typically a predetermined reference level, such as an average of levels obtained from a population that is not afflicted with AD or MCI. In some embodiments, the predetermined reference level is derived from (e.g., is the mean or median of) levels obtained from an age-matched or gender-matched population. Age-matched populations (from which reference values may be obtained) are ideally the same age as the individual being tested, but approximately age-matched population is also acceptable. Approximately age-matched populations may be in 2, 3, 4, 5, 6, 7, 8, 9, or 10 year increments (e.g., a "5 year increment" group which serves as the source for reference values for a 62 year old individual might include 58-62 year old individuals, 59-63 year old individuals, 60-64 year old individuals, 61-65 year old individuals, or 62-66 year old individuals).

For MCI diagnosis methods (i.e., methods of diagnosing or aiding the diagnosis of MCI), the reference level is typically a predetermined reference level, such as an average of levels obtained from a population that is not afflicted with AD or MCI. In some instances, the predetermined reference level is derived from (e.g., is the mean or median of) levels obtained from an age-matched or gender-matched population.

For AD monitoring methods (e.g., methods of monitoring treatment or disease progression in an AD patient), the reference level may be a predetermined level, such as an average of levels obtained from a population that is not afflicted with AD or MCI. Alternatively, the reference level may be a historical reference level for the particular patient (e.g., a carnosine level that was obtained from a sample derived from the same individual, but at an earlier point in time). In some instances, the predetermined reference level is derived from (e.g., is the mean or median of) levels obtained from an age-matched or gender-matched population.

For AD stratification methods (e.g., methods of stratifying AD patients into mild, moderate, and severe stages of AD), the reference level may be a predetermined reference level that is the mean or median of levels from a population which has been diagnosed with AD or MCI. In some instances, the predetermined reference level is derived from (e.g., is the mean or median of) levels obtained from an age-matched or gender-matched population.

As used herein, a "reference value" can be an absolute value; a relative value; a value that has an upper and/or lower limit; a range of values; an average value; a median value, a mean value, or a value as compared to a particular control or baseline value.

A comparison to a reference level may be performed for 1, 2, 3, 4, 5, 6, 7, 8, 9, 10, 20, 30, or more AD diagnosis markers. The process of comparing the levels of an AD diagnosis marker with a reference level can be carried out in any convenient manner appropriate to the type of measured values for the AD diagnosis marker at issue. For example, when a qualitative colorimetric assay is used to measure AD diagnosis marker levels, the levels may be compared by visually comparing the intensity of the colored reaction product, or by comparing data from densitometric or spectrometric measurements of the colored reaction product. For quantitative measures, the comparison can be made by inspecting the numerical data, inspecting representations of data (e.g., inspecting graphical representations such as bar or line graphs). The process of comparing may be manual (such as visual inspection by the practitioner of the methods) or it may be automated.

In some embodiments, the comparison is performed to determine the magnitude of the difference between the measured and reference levels (e.g., comparing the "fold" or percentage difference between the measured and reference levels). As used herein, the phrase "fold difference" refers to a numerical representation of the magnitude difference between a measured value and a reference value for an AD marker. Fold difference is calculated mathematically by division of the numeric measured value with the numeric reference value or measured value, whichever is bigger. For example, if a measured value for an AD marker is 600 nmol/dL, and the reference value is 300 nmol/dL, the fold difference is 50%. Alternatively, if a measured value for an AD marker is 300 nmol/dL, and the reference value is 600 nmol/dL, the fold difference is −50%. A fold difference can be determined by measuring the absolute concentration of the AD diagnosis marker and comparing that to the absolute concentration of the AD diagnosis marker in the reference, or a fold difference can be measured by the relative difference between a reference value and a sample value, wherein neither value is a measure of absolute concentration, and/or wherein both values are measured simultaneously.

A "characteristic change" in the levels of an AD diagnosis marker can simply be a decrease or increase in level of AD diagnosis marker in the individual as compared to a reference level. Table 5 provides a summary of changes of the listed AD diagnosis markers in one exemplary method. A characteristic change of the levels of the AD diagnostic markers are used as a basis for diagnosing AD. For example, in some embodiments when the CSF levels of at least one Group 1 AD diagnosis marker and at least one Group 2 AD diagnosis marker are determined, a decrease in the CSF levels of Group 1 AD diagnosis markers and/or an increase in the CSF levels of Group 2 AD diagnosis markers is indicative or suggestive of AD. In some embodiments when the plasma levels of at least one Group 3 AD diagnosis marker and at least one Group 4 AD diagnosis marker are determined, a decrease in the plasma levels of Group 3 AD diagnosis markers and/or an increase in the plasma levels of Group 4 AD diagnosis markers is indicative or suggestive of AD. In some embodiments when the urine levels of at least one Group 5 AD diagnosis marker and at least one Group 6 AD diagnosis markers are determined, a decrease in the urine levels of Group 5 AD diagnosis markers and/or an increase in the urine levels of Group 6 AD diagnosis markers is indicative or suggestive of AD. In some embodiments, when both the plasma and urine levels of carnosine are determined, a concomitant decrease in the plasma level of carnosine and an increase in the urine level of carnosine are indicative or suggestive of AD. In some embodiments when both the plasma and urine levels of carnosine and anserine are determined, a decrease in the plasma level of carnosine and urine level of anserine and a concomitant increase in the plasma level of anserine and a decrease in the urine level of anserine are indicative of AD.

In those embodiments utilizing fold difference values, a characteristic change can be represented by any one or more of the fold difference indicated in Tables 5. For example, in some embodiments, a fold change of −50% in the plasma level of carnosine is indicative of AD.

In some embodiments when more than one AD diagnosis markers are used but the markers do not unanimously suggest or indicate a diagnosis of AD, the "majority" suggestion or indication may be considered the result of the assay. For example, when the method utilizes five AD diagnosis markers, 3 of which suggest/indicate AD, the result may be considered as suggesting or indicating a diagnosis of AD for the individual. However in some embodiments, a diagnosis of AD requires a characteristic change of at least one, or more, specific AD diagnosis marker(s). For example, in cases when one of the AD diagnosis marker is carnosine, a decreased level of carnosine in some embodiments may be a prerequisite for a diagnosis of AD. In cases when both carnosine and dopamine are determined, a decreased levels of both carnosine and dopamine in some embodiments may be a prerequisite for a diagnosis of AD.

Figure 8:
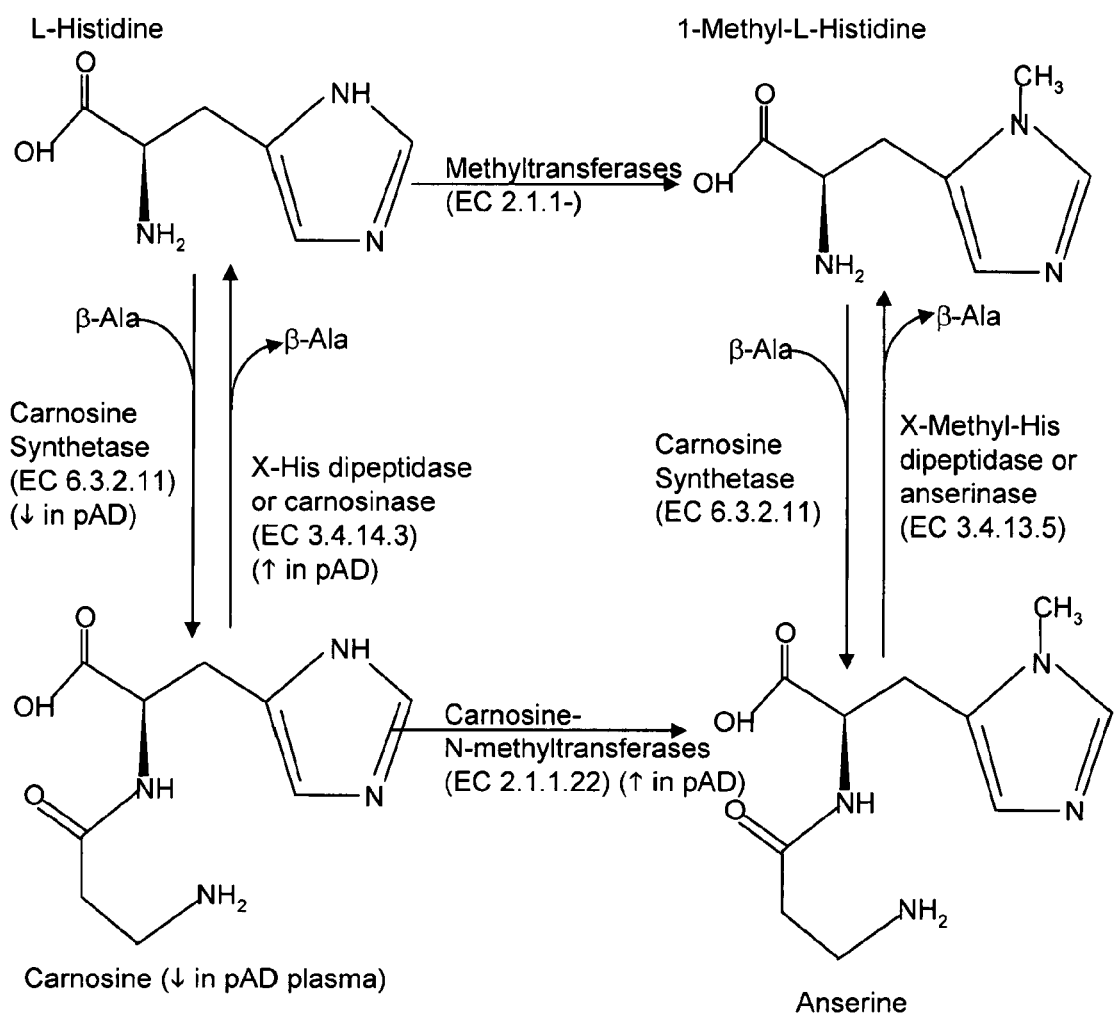
FIG. 8 shows the biochemical pathway of histidine metabolism. Arrows stands for the proposed changes (up arrows for increase, down arrows for decrease) in free amino acids and dipeptides in body fluids (e.g., plasma) and the proposed changes in enzyme activity and/or levels that likely account for these changes.

Methods of Diagnosing and Treating AD Based on Changes in Carnosine Biosynthesis Pathway The invention in another aspect provides a method of diagnosing AD based on. changes in the biochemical pathway that leads to an increased level of carnosine. A correlation between AD and a decrease in carnosine level in the plasma was observed. In addition, there is an increase in plasma anserine in AD patients. These changes suggest a link between carnosine biosynthesis pathway and AD. For example, carnosine synthesis activities may be lower in AD patients as compared to normal individuals, or the rate of carnosine degradation by carnosinase is higher in AD patients as compared to normal individuals (FIG. 8). These enzymatic activities (relative or absolute) may therefore also serve as indicators of AD.

Accordingly, in some embodiments, there is provided a method of diagnosing AD in an individual, comprising: a) comparing the plasma level of carnosine of the individual with a reference level, and b) determining whether the individual has AD based on a decrease in the plasma level of carnosine. For example, in some embodiments, a decrease in the plasma level of carnosine by at least about any of 20%, 30%, 40%, 50%, 60%, 60%, 70%, or more, is indicative of AD. In some embodiments, the method further comprises comparing the plasma levels of histidine, 1-methyl-L-histidine, and anserine with a reference level, wherein a characteristic change of one or more of these free amino acids or dipeptides are used as a basis for diagnosing AD.

In some embodiments, changes in the activities of carnosine synthetase, carnosine-N-methyltransferase, and/or carnosinase are used as indicators of AD. For example, in some embodiments, the method comprises: a) comparing the relative activity of carnosinase (or carnosine-N-methyltransferase) versus carnosine synthetase in the plasma of the individual with a reference relative activity, and b) determining whether the individual has AD based on an increase in the relative activity. In some embodiments, an increase in the relative activity of carnosinase versus carnosine synthetase by at least about any of 20%, 30%, 40%, 50%, 60%, 60%, 70%, or more, is indicative of AD. In some embodiments, the method comprises: a) comparing the activity of carnosine synthetase in the plasma of the individual with a reference activity, and b) determining whether the individual has AD based on a decrease in the activity of carnosine synthetase. In some embodiments, a decrease in the activity of carnosine synthetase by at least about any of 20%, 30%, 40%, 50%, 60%, 60%, 70%, or more, is indicative of AD. In some embodiments, the method comprises: a) comparing the activity of carnosinase or carnosine-N-methyltransferase in the plasma of the individual with a reference activity, and b) determining whether the individual has AD based on an increase in the activity of carnosinase or carnosine-N-methyltransferase. In some embodiments, an increase in the activity of carnosinase or carnosine-N-methyltransferase by at least about any of 20%, 30%, 40%, 50%, 60%, 60%, 70%, or more, is indicative of AD. The methods described herein may further comprise providing a plasma sample from the individual and/or determining the activities of at least one of carnosine synthetase, carnosinase, and carnosine-N-methyltransferase in the plasma.

The present invention also encompasses methods of providing information about levels of carnosine and/or activities of one or more of carnosine synthetase, carnosinase, and carnosine-N-methyltransferase. Such information can then be used for diagnosis of AD. Accordingly, in some embodiments, there is provided a method comprising: a) determining the plasma level of carnosine in the individual, and b) providing information about the plasma level of carnosine, wherein the plasma level of carnosine is used as basis for diagnosing AD, and wherein a decrease in the plasma level of carnosine is indicative of AD. In some embodiments, there is provided a method comprising: a) determining the relative activity of carnosinase (and carnosine-N-methyltransferase versus carnosine synthetase in the plasma of the individual, and b) providing information about the relative activity, wherein the relative activity of carnosinase versus carnosine synthetase in the plasma is used as a basis for diagnosing AD, and wherein an increase in the relative activity is indicative of AD. In some embodiments, there is provided a method comprising: a) determining the activity of carnosine synthetase in the plasma of the individual, and b) providing information about the carnosine synthetase activity, wherein the carnosine synthetase activity in the plasma is used as a basis for diagnosing AD, and wherein a decrease in carnosine synthetase activity in the plasma is indicative of AD. In some embodiments, there is provided a method comprising: a) determining the activity of carnosinase or carnosine-N-methyltransferase in the plasma of the individual, and b) providing information about the enzyme activity, wherein the carnosinase or carnosine-N-methyltransferase activity in the plasma is used as a basis for diagnosing AD, and wherein an increase in carnosinase or carnosine-N-methyltransferase activity in the plasma is indicative of AD.

As will be understood by a person skilled in the art, the methods described herein are also useful for one or more of the following: aiding diagnosis of AD, predicting risk of developing AD, monitoring AD progression in AD patients, monitoring AD treatment in AD patients, stratifying AD patients, assessing cognitive function, assessing cognitive impairment, and diagnosing or aiding diagnosis of mild cognitive impairment (MCI), and diagnosing or aiding diagnosis of cognitive impairment.

The plasma levels of carnosine and carnosine synthesis activities may also be used as a basis for selecting the individual to receive or continuing to receive treatment. Specifically, plasma levels of carnosine and carnosine synthesis activities may be used as a basis by a clinician in assessing any of the following: (a) probable or likely suitability of an individual to initially receive treatment(s); (b) probable or likely unsuitability of an individual to initially receive treatment(s); (c) responsiveness to treatment(s); (d) probable or likely suitability of an individual to continue to receive treatment(s); (e) probable or unsuitability of an individual to continue to receive treatment(s); (f) adjusting dosage(s); (g) predicting likelihood of clinical benefits. As would be well understood by one in the art, measurement of plasma levels of carnosine and/or carnosine synthesis activities may be a clear indication that this parameter is used as a basis for initiating, continuing, adjusting and/or ceasing administration of the treatments described herein.

As used herein, the term "treatment" refers to the alleviation, amelioration, and/or stabilization of symptoms, as well as delay in progression of symptoms of a particular disorder. For example, "treatment" of AD includes any one or more of elimination of one or more symptoms of AD, reduction of one or more symptoms of AD, stabilization of the symptoms of AD (e.g., failure to progress to more advanced stages of AD), and delay in progression (i.e., worsening) of one or more symptoms of AD.

In some embodiments, there is provided a method of treating AD in an individual, comprising administering to the individual an effective amount of an agent that increases the plasma level of carnosine, wherein diagnosis of AD is based on a decrease in the plasma level of carnosine in the individual as compared to a reference level. In some embodiments, there is provided a method of treating AD in an individual, comprising: a) determining whether the individual has AD based on a decrease in the plasma level of carnosine in the individual as compared to a reference level, and b) administering to the individual an effective amount of an agent that increases the plasma level of carnosine. In some embodiments, the method further comprises monitoring the levels of plasma carnosine level and determining whether the individual is suitable for continued treatment with an agent that increases the plasma level of carnosine. In some embodiments, the method further comprises continuing to treat the individual with an agent that increases the plasma level of carnosine.

Agents that increase the plasma level of carnosine include, for example, carnosine itself, enhancers of carnosine synthetase activity (such as carnosine analogs), inhibitors of carnosinase, inhibitors of carnosine-N-methyltransferase, and agents that delay the clearance of carnosine (such as modifiers of carnosine). The methods described herein encompass use of any of these agents.

Accordingly, in some embodiments, there is provided a method of treating AD in an individual, comprising administering to the individual an effective amount of an agent that inhibits the activity of carnosinase or an agent that enhances the activity of carnosine synthetase in the plasma. In some embodiments, there is provided a method of treating AD in an individual, comprising: a) determining whether the individual has AD based on a decrease in the plasma level of carnosine in the individual as compared to a reference level, and b) administering to the individual an effective amount of an agent that inhibits the activity of carnosinase or an agent that enhances the activity of carnosine synthetase in the plasma. In some embodiments, there is provided a method of treating AD in an individual, comprising: a) determining whether the individual has AD based on the relative activity of carnosinase versus carnosine synthetase in the plasma of the individual, and b) administering to the individual an effective amount of an agent that inhibits the activity of carnosinase or an agent that enhances the activity of carnosine synthetase in the plasma.

Methods of Diagnosing and Treating AD Based on Changes in Dopamine Synthesis

Figure 9:
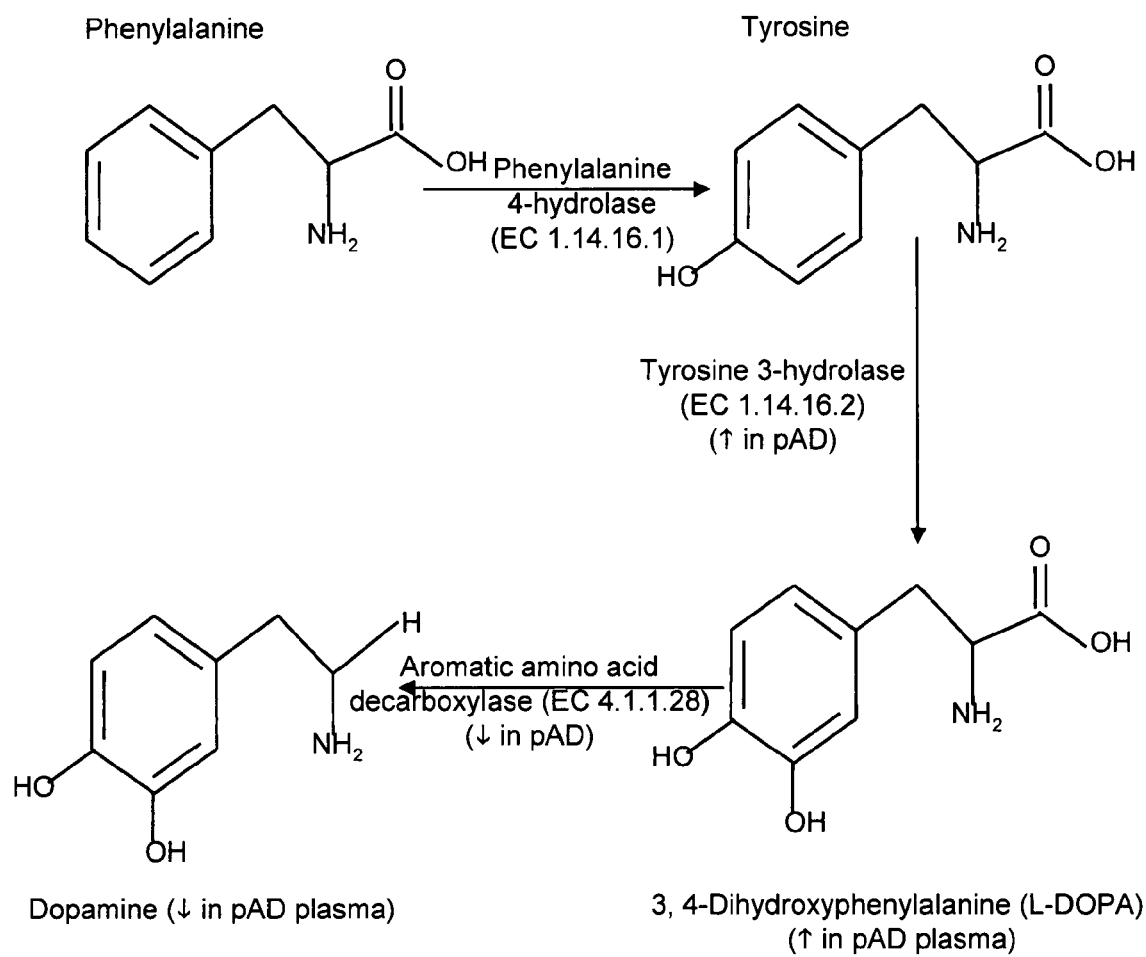
FIG. 9 shows the biochemical pathway of dopamine metabolism. Arrows stands for the proposed changes (up arrows for increase, down arrows for decrease) in free amino acids and dipeptides in body fluids (e.g., plasma) and the proposed changes in enzyme activity and/or levels that likely account for these changes.

In another aspect, there is provided a method of diagnosing and treating Alzheimer's disease ("AD") based on the plasma level of dopamine or DOPA or the enzymatic activities in the dopamine synthesis pathway. As described above, the plasma level of DOPA is significantly increased in AD patients while the plasma level of dopamine is decreased. Biochemical changes that may account for the decrease in plasma dopamine concomitant with the increase in DOPA include an increase in tyrosine hydrolase activity and/or a decrease in DOPA decarboxylase activity in the plasma of AD patients (FIG. 9).

Accordingly, in some embodiments, there is provided a method of diagnosing AD in an individual, comprising: a) comparing the plasma level of dopamine of the individual with a reference level, and b) determining whether the individual has AD based on a decrease in the plasma level of dopamine. In some embodiments, a decrease in the plasma level of dopamine by at least about any of 5%, 10%, 15%, 20%, 25%, or more is indicative of AD. In some embodiments, there is provided a method of diagnosing AD in an individual, comprising: a) comparing the plasma level of DOPA of the individual with a reference level, and b) determining whether the individual has AD based on an increase in the plasma level of DOPA. In some embodiments, an increase in the plasma level of DOPA by at least about 20%, 30%, 40%, 50%, 60%, 70%, or more, is indicative of AD. In some embodiments, the diagnosis of AD is based on an increase in the plasma level of DOPA and a concomitant decrease in the plasma level of dopamine. For example, in some embodiments, an increase in the plasma level of DOPA by at least about any of 20%, 30%, 40%, 50%, 60%, 70%, or more, and a decrease in the plasma level of dopamine by at least about any of 5%, 10%, 15%, 20%, 25%, or more, is indicative of AD. In some embodiments, the method further comprises comparing the plasma levels of phenylalanine and tyrosine, wherein a characteristic change of one or more of these free amino acids are used as a basis for diagnosing AD.

In some embodiments, there is provided a method of diagnosing AD in an individual, comprising: a) comparing the relative activity of tyrosine-3-hydrolase versus DOPA decarboxylase in the plasma of the individual with a reference relative activity, and b) determining whether the individual has AD based on an increase in the relative activity. In some embodiments, an increase in the relative activity of tyrosine-3-hydrolase versus DOPA decarboxylase in the plasma by at least about any of 20%, 30%, 40%, 50%, 60%, 60%, 70%, or more, is indicative of AD. In some embodiments, there is provided a method of diagnosing AD in an individual, comprising: a) comparing the activity of DOPA decarboxylase in the plasma of the individual with a reference activity, and b) determining whether the individual has AD based on a decrease in the activity of DOPA decarboxylase. In some embodiments, a decrease in the activity of DOPA decarboxylase by at least about any of 20%, 30%, 40%, 50%, 60%, 60%, 70%, or more, is indicative of AD. In some embodiments, there is provided a method of diagnosing AD in an individual, comprising: a) comparing the activity of tyrosine-3-hydrolase in the plasma of the individual with a reference activity, and b) determining whether the individual has AD based on an increase in the activity of tyrosine-3-hydrolase. In some embodiments, an increase in the activity of tyrosine-3-hydrolase by at least about any of 20%, 30%, 40%, 50%, 60%, 60%, 70%, or more, is indicative of AD.

The present invention also encompasses methods of providing information about the levels of dopamine or DOPA, and/or activities of DOPA decarboxylase and/or tyrosine-3-hydrolase. Such information can then be used for diagnosis of AD. Accordingly, in some embodiments, there is provided a method comprising: a) determining the plasma level of dopamine and/or DOPA in the individual, and b) providing information about the plasma level of dopamine and/or DOPA, wherein the plasma level of dopamine and/or DOPA is used as basis for diagnosing AD, and wherein an increase in the plasma level of dopamine, and decrease in the plasma level of DOPA, or both, is indicative of AD. In some embodiments, there is provided a method comprising: a) determining the relative activity of tyrosine-3-hydrolase versus DOPA decarboxylase in the plasma of the individual, and b) providing information about the relative activity, wherein the relative activity of tyrosine-3-hydrolase versus DOPA decarboxylase in the plasma is used as a basis for diagnosing AD, and wherein an increase in the relative activity is indicative of AD. In some embodiments, there is provided a method comprising: a) determining the activity of tyrosine-3-hydrolase in the plasma of the individual, and b) providing information about the tyrosine-3-hydrolase activity, wherein the tyrosine-3-hydrolase activity in the plasma is used as a basis for diagnosing AD, and wherein an increase in tyrosine-3-hydrolase activity in the plasma is indicative of AD. In some embodiments, there is provided a method comprising: a) determining the activity of DOPA decarboxylase in the plasma of the individual, and b) providing information about the enzyme activity, wherein the DOPA decarboxylase activity in the plasma is used as a basis for diagnosing AD, and wherein a decrease in the DOPA decarboxylase activity in the plasma is indicative of AD.

As will be understood by a person skilled in the art, the methods described herein are also useful for one or more of the following: aiding diagnosis of AD, predicting risk of developing AD, monitoring AD progression in AD patients, monitoring AD treatment in AD patients, stratifying AD patients, assessing cognitive function, assessing cognitive impairment, diagnosing or aiding diagnosis of mild cognitive impairment (MCI), and diagnosing or aiding diagnosis of cognitive impairment.

The plasma level of DOPA, dopamine, dopamine synthesis activities may also be used as a basis for selecting the individual to receive or continuing to receive treatment. Specifically, plasma level of DOPA, dopamine, and dopamine synthesis activities may be used as a basis by a clinician in assessing any of the following: (a) probable or likely suitability of an individual to initially receive treatment(s); (b) probable or likely unsuitability of an individual to initially receive treatment(s); (c) responsiveness to treatment(s); (d) probable or likely suitability of an individual to continue to receive treatment(s); (e) probable or unsuitability of an individual to continue to receive treatment(s); (f) adjusting dosage(s); (g) predicting likelihood of clinical benefits. As would be well understood by one in the art, measurement of plasma levels of dopamine, DOPA, and dopamine synthesis activities may be a clear indication that this parameter is used as a basis for initiating, continuing, adjusting and/or ceasing administration of the treatments described herein.

In some embodiments, there is provided a method of treating AD in an individual, comprising administering to the individual an effective amount of an agent that increases the plasma level of dopamine or decreases the level of DOPA, wherein diagnosis of AD is based on a decrease in the plasma level of dopamine or an increase in the plasma level of DOPA in the individual as compared to a reference level. In some embodiments, there is provided a method of treating AD in an individual, comprising: a) determining whether the individual has AD based on a decrease in the plasma level of dopamine or an increase in the plasma level of DOPA in the individual as compared to a reference level, and b) administering to the individual an effective amount of an agent that increases the plasma level of dopamine or decreases the level of DOPA. In some embodiments, the method further comprises monitoring the levels of plasma dopamine or DOPA level and determining whether the individual is suitable for continued treatment with an agent that increases the plasma level of dopamine or an agent that decreases the plasma level of DOPA. In some embodiments, the method further comprises continuing to treat the individual with an agent that increases the plasma level of dopamine or an agent that decreases the plasma level of DOPA.

Agents that increase the plasma level of dopamine include, for example, dopamine itself, agents that inhibit the activity of tyrosine-L-transferase, agents that enhance the activity of DOPA decarboxylase, dopamine receptor agonists (such as bromocriptine), and agents that retards degradation of dopamine (such as selegiline). In some embodiments, there is provided a method of treating AD in an individual, comprising administering to the individual an effective amount of an agent that inhibits the activity of tyrosine-L-transferase or an agent that enhances the activity of DOPA decarboxylase activity in the plasma. In some embodiments, there is provided a method of treating AD in an individual, comprising: a) determining whether the individual has AD based on a decrease in the plasma level of dopamine and/or an increase in the plasma level of DOPA in the individual as compared to a reference level, and b) administering to the individual an effective amount of an agent that inhibits the activity of tyrosine-L-transferase or an agent that enhances the activity of DOPA decarboxylase activity in the plasma. In some embodiments, there is provided a method of treating AD in an individual, comprising: a) determining whether the individual has AD based on an increase in the relative activity of tyrosine-3-hydrolase versus DOPA decarboxylase in the plasma of the individual, and b) administering to the individual an effective amount of an agent that inhibits the activity of tyrosine-L-transferase or an agent that enhances the activity of DOPA decarboxylase activity in the plasma.

Methods of Determining Levels of Free Amino Acids and Dipeptides Using LCMS$^2$

In another aspect, there is provided a method of determining the level(s) of free amino acids or dipeptides in a biological fluid sample using liquid chromatography tandem mass spectrometry (LCMS$^2$) method. LCMS$^2$ method is known and has been described in, for example, Jansen et al., *J. Chromatography B*, 830:196-200 (2006); Bourcier et al., *Rapid Commun. Mass Spectrom.* 2006, 20(9):1405-21.

We have found that, by combining sample preparation with liquid chromatography and optimizing various parameters for each free amino acid and dipeptides and using internal standards, LCMS$^2$ can be used to determine the concentrations of many free amino acids and dipeptides that vary in concentration over many thousand folds in the same sample. In one exemplary method, serial dilutions (0-100 μmol) of free amino acids and dipeptides is carried out with a constant amount (50 μmol) of deuterated internal standard added to each standard. 50 μmol deuterated internal standard is also added to 100-400 ul body fluids (plasma, urine, or CSF) to monitor recovery and for quantification. Free amino acids and dipeptides are extracted from biological fluid samples using solid phase extraction and are derivatized to chloroformate derivatives using the EZFaast kit from Phenomenex. Precursor ions (m/z) of each free amino acids and dipeptides are determined using positive ion ESI/MS. Tandem MS is used to obtain the major product ions, which are verified using a product ion scan followed by fragmentation by increasing collisional induced dissociation (CID) pressure. Mechanism of formation of specific products is verified using Mass Frontier software (ThermoElectron). For the most intense product, we perform precursor ion to product ion transitions by selective reaction monitoring (SRM) using collision energy (CE) and tube lens voltage as variables. All other mass spectrometry parameters are similarly maintained for all free amino acids and dipeptides. We generate SRM tables used for developing LCMS$^2$ method, development of processing method and LC-Quan methods. Serial dilution of standard are tested to obtain standard curves. Unknown samples from body fluids are run (either before or after the standards are run) to obtain the ratio of unlabeled ion intensities to the intensities of deuterated internal standards. The quantities of free amino acids and dipeptides in a biological body fluid can then be calculated using linear equations from standards.

The method provided herein is very sensitive with very low limit of detection (LOD), requiring small amounts of body fluids. The sensitivity and specificity of this technology makes it possible to simultaneously determine the levels of at least two, or more, free amino acids or dipeptides in a single biological fluid sample, thus allowing for simultaneous determination of metabolites and enzymes that are altered. The approach also has broad application in the study of metabolic diseases or of biochemical pathways that involve changes in the concentrations of several metabolites.

Accordingly, in some embodiments, there is provided a method of simultaneously measuring the levels of at least two free amino acids or dipeptides in a biological fluid sample, comprising subjecting the sample to LCMS$^2$, wherein the levels of at least two (such as at least any of 3, 5, 10, 15, 20, 30, 40, 50, 60, 70, 80, or more) free amino acids or dipeptides (such as free amino acids or dipeptides identified in Table 1) are determined. The term "simultaneously" used herein refers to the fact that the levels of two or more free amino acids or dipeptides are detected from a single biological fluid sample for the LCMS$^2$ experiment. In some embodiments, the levels of at least two (such as at least 3, 5, 10, 15, 20, 30, 40, 50, 60, 70, 80, or more) free amino acids or dipeptides are used for diagnosis of a disease, such as AD.

In some embodiments, there is provided a method of assessing changes in levels of at least two free amino acids or dipeptides in a biological body fluid sample, comprising detecting level of at least one (such as at least any of 3, 5, 10, 20, 30, 40, 50, 60, 70, 80, or more) free amino acid or dipeptide (such as free amino acids or dipeptides identified in Table 1) in the sample by LCMS$^2$ method and comparing the detected levels with reference levels. In some embodiments, a characteristic change in at least one (such as at least any of 2, 3, 5, 10, 20, or more) of the free amino acids or dipeptides are indicative of a disease, such as AD.

TABLE 1

| Amino acids and dipeptides | Parent ions (m/z) | Product ions (m/z) | Collision energy (v) | Tube lens voltage | Correlation ($R^2$) | Deviation (% mean) | LOD (pmol) |
|---|---|---|---|---|---|---|---|
| Ethanolamine | 148.00 | 106.00 | 47 | 68 | 0.39 | 0.81 | ND |
| Pyroglutamic Acid | 172.00 | 130.00 | 10 | 165 | 0.88 | 15.74 | 0.5 |
| Serine | 234.00 | 174.00 | 10 | 101 | 0.94 | 2.21 | 0.05* |
| Glutamine | 275.00 | 172.00 | 18 | 103 | 0.93 | 3.84 | 0.05* |
| Arginine | 303.00 | 200.00 | 24 | 98 | 0.92 | 4.21 | 0.2 |
| Citrulline | 304.00 | 244.00 | 10 | 98 | 0.93 | 3.99 | 0.05 |
| Homo-phenylalanine | 308.00 | 117.10 | 42 | 111 | IS | IS | IS |
| Homoarginine | 317.00 | 170.00 | 28 | 107 | IS | IS | IS |
| Phospho-threonine | 325.00 | 117.00 | 60 | 65 | | | |
| Anserine | 369.00 | 212.00 | 37 | 103 | 0.97 | 2.16 | 0.2 |
| Acetylcholine | 148.08 | 87.07 | 18 | 61 | 0.82 | 17.22 | 0.6 |
| Glycine | 204.00 | 118.00 | 47 | 63 | 0.92 | 5.28 | 0.05 |
| Asparagine | 243.00 | 157.00 | 33 | 90 | 0.73 | 7.68 | 0.2 |
| Asparagine | 243.00 | 201.00 | 22 | 102 | | | |
| Threonine | 248.00 | 160.00 | 18 | 133 | 0.95 | 4.03 | 0.4 |
| 4-Hydroxyproline | 260.00 | 172.00 | 18 | 88 | 0.85 | 7.80 | 0.5*** |
| 2-Methylhistidine | 298.00 | 210.00 | 26 | 100 | 0.96 | 1.88 | 0.05* |
| 1-Methylhistidine | 298.00 | 256.00 | 27 | 100 | 0.96 | 2.16 | 0.05* |
| Glycine-proline | 301.00 | 158.00 | 20 | 110 | 0.89 | 8.21 | 0.05*** |
| β-Alanine | 218.00 | 116.00 | 22 | 73 | 0.22 | 66.40 | ND |
| Alanine | 218.00 | 130.00 | 21 | 73 | 0.93 | 2.05 | 0.5 |
| 4-Aminobutyric acid | 232.00 | 130.00 | 17 | 103 | 0.71 | 13.50 | 0.5 |
| α-Aminobutyric acid | 232.00 | 144.00 | 10 | 103 | 0.72 | 22.12 | 1 |

TABLE 1-continued

| Amino acids and dipeptides | Parent ions (m/z) | Product ions (m/z) | Collision energy (v) | Tube lens voltage | Correlation (R²) | Deviation (% mean) | LOD (pmol) |
|---|---|---|---|---|---|---|---|
| β-Aminobutyric acid | 232.00 | 172.00 | 10 | 103 | 0.65 | 26.94 | 0.5 |
| Histamine | 284.00 | 138.00 | 25 | 89 | 0.75 | 9.91 | 0.5 |
| 2,4-Diaminobutyric acid | 333.00 | 273.00 | 10 | 103 | 0.85 | 12.06 | 0.4 |
| Ornithine | 347.00 | 201.00 | 22 | 97 | 0.82 | 9.087 | 0.5 |
| Proline-hydroxyproline | 357.00 | 156.00 | 21 | 127 | 0.94 | 2.26 | 0.05*** |
| Proline | 244.00 | 156.00 | 15 | 100 | 0.96 | 2.76 | 0.2 |
| Methionine | 278.00 | 190.00 | 27 | 90 | 0.66 | 32.44 | ND |
| [²H₃]-Methionine | 281.00 | 193.00 | 10 | 75 | IS | IS | IS |
| Aspartic acid | 304.00 | 216.00 | 21 | 108 | 0.95 | 3.08 | 0.2 |
| Phosphothreonine | 325.20 | 117.00 | 57 | 60 | | | |
| Lysine | 361.00 | 170.00 | 25 | 119 | 0.85 | 11.73 | 2 |
| Histidine | 370.00 | 196.00 | 28 | 93 | 0.88 | 0.65 | 0.5** |
| Lysine-alanine | 432.00 | 170.00 | 36 | 120 | 0.96 | 1.72 | 0.05** |
| Carnosine | 441.00 | 284.00 | 26 | 92 | 0.93 | 5.95 | 0.8 |
| Homoserine | 230.00 | 188.00 | 10 | 140 | 0.88 | 14.32 | 0.05 |
| Valine | 246.00 | 156.00 | 18 | 97 | 0.95 | 1.28 | 0.05 |
| Thioproline | 262.00 | 174.00 | 17 | 109 | 0.96 | 1.24 | 0.05 |
| Ethionine | 292.00 | 204.00 | 10 | 85 | 0.96 | 0.83 | 0.05 |
| Glutamic acid | 318.00 | 172.00 | 27 | 91 | 0.94 | 1.44 | 0.05** |
| α-Aminoadipic acid | 332.00 | 244.00 | 19 | 107 | 0.94 | 0.74 | 0.05** |
| Tryptophan | 333.00 | 230.00 | 20 | 75 | 0.96 | 1.96 | 0.05** |
| γ-Glutamyl-ε-lysine | 532.00 | 414.00 | 17 | 91 | 0.93 | 1.06 | 0.1 |
| Isoleucine | 260.00 | 130.00 | 26 | 81 | 0.94 | 0.55 | 0.05* |
| Leucine | 260.00 | 172.00 | 18 | 81 | 0.94 | 0.73 | 0.05*** |
| Allo-isoleucine/Norleucine | 260.00 | 200.00 | 17 | 86 | 0.93 | 2.29 | 0.4 |
| Phenylalanine | 294.00 | 106.00 | 10 | 52 | 0.94 | 0.33 | 0.05* |
| Cysteine | 336.00 | 190.00 | 37 | 71 | 0.93 | 4.87 | 0.05* |
| Aminopimelic acid | 346.00 | 156.00 | 27 | 85 | 0.94 | 1.58 | 0.05* |
| Adrenaline | 424.00 | 252.00 | 21 | 148 | 0.95 | 2.27 | 0.05* |
| Noradrenaline | 445.48 | 107.02 | 53 | 95 | 0.94 | 5.12 | 0.1 |
| 4-Aminobenzoic acid | 266.00 | 224.00 | 21 | 89 | 0.96 | 3.30 | 0.5 |
| Homophenylalanine | 308.00 | 117.00 | 38 | 102 | IS | IS | IS |
| Homocysteine | 350.00 | 204.00 | 18 | 92 | 0.97 | 2.22 | 0.5 |
| Tyrosine | 396.00 | 294.00 | 10 | 74 | 0.96 | 0.77 | 0.1* |
| Dopamine | 412.00 | 266.00 | 19 | 82 | 0.96 | 2.14 | 0.1* |
| Cystathionine | 479.00 | 230.00 | 21 | 131 | 0.94 | 0.84 | 0.05* |
| Cystine | 497.00 | 248.00 | 19 | 103 | 0.95 | 1.81 | 0.05 |
| Homocystine | 525.00 | 262.00 | 21 | 97 | 0.91 | 1.91 | 0.05** |
| 3-Nitro-L-tyrosine | 534.23 | 94.01 | 53 | 94 | 0.89 | 5.60 | 0.1 |
| Urea | 117.00 | 72.00 | 17 | 57 | | | |
| Sarcosine | 218.15 | 88.08 | 22 | 82 | 0.74 | 15.63 | 1 |
| Phosphoserine | 317.21 | 84.10 | 42 | 94 | | | |
| [¹⁵N]-Glutamic Acid | 319.17 | 85.06 | 37 | 101 | IS | IS | IS |
| Noradrenaline | 445.24 | 152.03 | 38 | 85 | | | |
| Phosphotyrosine | 498.00 | 412.00 | 26 | 99 | 0.92 | 4.30 | 0.05* |
| L-Phenylalanine | 294.18 | 120.06 | 37 | 89 | 0.94 | 0.89 | 0.05*** |
| Melatonin | 326.00 | 94.00 | 41 | 65 | 0.86 | 5.95 | 0.05 |
| Seretonin | 349.16 | 160.04 | 38 | 93 | 0.93 | 4.25 | 0.05*** |
| 3-Hydroxytyramine | 429.25 | 137.11 | 38 | 75 | 0.91 | 3.19 | 0.05*** |
| 3-Chloro-L-tyrosine | 447.24 | 170.01 | 37 | 102 | 0.97 | 0.74 | 0.05*** |
| L-DOPA | 515.29 | 178.02 | 42 | 98 | 0.97 | 2.96 | 0.2 |
| [²H₃]-L-DOPA | 518.29 | 180.02 | 47 | 119 | IS | IS | IS |
| 2,4,5-Trihydroxy-DL-phenylalanine | 600.32 | 149.93 | 42 | 107 | 0.87 | 6.66 | 0.2 |

In some embodiments, there is provided a method of identifying one or more diagnosis markers of a disease, comprising simultaneously measuring the levels of at least two free amino acids or dipeptides (such as free amino acids or dipeptides identified in Table 1) from a set of biological fluid samples by LCMS$^2$, wherein the set of biological fluid samples is divisible into subsets on the basis of a disease, comparing the levels from each subset for at least one biomarker, and identifying at least one marker for which the levels are significantly different between the two subsets. In some embodiments, the method comprises simultaneously measuring the levels of at least 2, 3, 5, 10, 20, 30, 40, 50, 60, 70, 80, or more free amino acids or dipeptides. In some embodiments, the disease is AD.

Analysis of levels of free amino acids or dipeptides are also useful in elucidating the biochemical pathways underlying a given disease pathology. The present invention therefore also provide methods of determining a biochemical pathway underlying a disease pathology, comprising simultaneously measuring the levels of at least two free amino acids or dipeptides (such as free amino acids or dipeptides identified in Table 1) from a set of biological fluid samples of an individual having a disease by LCMS$^2$, wherein the levels of the free amino acids or dipeptides indicate or suggest the involvement of a biochemical pathway underlying the disease pathology.

The following Examples are provided to illustrate, but not limit, the invention.

Example 1

This example shows quantification of free amino acids ("FAAs") and dipeptides ("DPs") using isotopic dilution liquid chromatography and electrospray ionization tandem mass spectrometry.

Materials and Methods

Ammonium formate, ultrapure HPLC grade water and methanol were bought from VWR (West Chester, Pa.). The EZ-Faast amino acid analyses kit containing sorbent extraction tips, extraction solutions, amino acid standards, derivatization reagents and C18 liquid chromatography column, was bought from Phenomenex (Torrance, Calif.). Bovine serum albumin and FAA standards including the internal standard ([$^2$H$_3$]-L-DOPA, [$^{15}$N]-glutamine) not provided in the EZ-Faast kit were bought from Sigma (St Louis, Mo.). Protein dye reagent concentrate was from BioRad Laboratories (Hercules, Calif.).

Study participants who gave informed consent were recruited prospectively from the North Los Angeles area for our IRB-approved research. These subjects had no classifiable brain disorder after complete neurological and psychiatric evaluation. Comorbid conditions such as hypertension were recorded but were not a reason for exclusion.

We collected CSF by lumbar punctures performed by a neurologist between 1-5 pm, either in the lateral or sitting positions, using a 22 gauge Quincke type needle, between either the L3/4 or L2/3 positions. CSF was drip collected in three consecutive fractions (~7 mL each), centrifuged at 3000×g to pellet cells, fractionated into 1.0 ml aliquots and stored at −80° C.

Whole blood (~10 mL) was collected by venipuncture into anticoagulant (K$_3$ EDTA vacutainers, Becton Dickinson) and centrifuged at 3000×g to separate plasma from blood cells. Plasma fractions (0.5 mL) were stored at −80° C.

Approximately 30 mL of midstream urine was collected during the same visit as CSF and plasma collections. Urine samples were centrifuged at 3000×g to remove particulates, fractionated into 5 ml aliquots and stored at −80° C. until needed for analysis.

The extraction and derivatization of FAA procedure consisted of a solid phase extraction step, followed by a derivatization procedure using the EZ-Faast amino acid analyses kit from Phenomenex. Briefly, internal standards were added to plasma (100 µl), CSF (200 µl) or urine (200 µl) and FAAs and DPs were extracted using Sorbent Tips and reagents from the EZ-Faast kit following the instructions of the kit's manufacturer (Phenomenex). Extracted FAAs and DPs were converted to chloroformates (Husek, 1998) and analyzed by LC tandem MS as described below.

In the LCMS$^2$ experiment, precursor ions of FAAs and DPs were obtained using a full scan MS infusion experiment. Tandem MS was used to obtain the most intense product ion from each FAA and DP. Selected reaction monitoring (SRM) parameters (collision energy and tube lens voltage) were optimized for each FAA and DP. FAAs (10 µl) were then separated using a C18 Luna HPLC column (2 mm×250 mm, maintained at 45° C.) on an HP1100 liquid chromatography system (Agilent, Palo Alto, Calif.). FAAs were eluted from the column using a linear methanol gradient starting with water:methanol (32/68 v/v) containing 10 mM ammonium formate at 0.2 ml/min over 10 min. The total run time including column equilibration was 35.5 min. The HPLC eluent was directly interphased to the electrospray ionization (ESI) source of a triple quadrupole mass spectrometer (TSQ Quantum from Thermo Electron, San Jose, Calif.) operated at a spray voltage of 4500 V, sheath Gas pressure of 30 units, auxiliary gas pressure of 0, capillary temperature of 300° C. and collision pressure of 1.5 units. Positive ions were acquired in the profile mode with 7 different scan events using SRM after collision-induced dissociation (10 V) of protonated or ammonium precursor ions. All SRM transition peak intensities were integrated, processed and mole quantities determined using ICIS and Xcalibur software, respectively (Thermo Electron). Mole quantities were determined from standard curves obtained using known amounts of FAA and DP (0-100 pmol) standards and 100 pmol internal standards ([$^2$H$_3$]-L-DOPA, [$^2$H$_3$]-methionine, [$^{15}$N]-glutamine, homoarginine, homophenylalanine). The ratio of FAA or DP peak area to IS peak area was obtained and a linear equation relating mole amounts of FAA to this ratio was obtained. This linear equation was then used to calculate the mole quantities of each FAA or DP in CSF, plasma and urine.

Statview (Abacus Concepts, Berkeley, Calif.) was used to calculate mean concentrations and LOD values, determine linear equations and correlation (r$^2$) of standard curves of FAAs and DPs.

Results

Detection of FAAs and DPs by LCMS$^2$

We used LC-positive ion-electrospray ionization tandem MS with SRM for these studies. Chloroformate derivatives were obtained for each FAA and DP and precursor ions were identified. MS2 was performed to obtain the most intense product ions. A precursor ion-product ion transition optimization was performed for each metabolite (Table 1). As shown on Table 1, columns 2-5, each FAA and DP displayed a distinct precursor ion-product ion transition that made it possible to selectively detect each of them in our samples. For FAAs with the same parent ion m/z such as 1 methyl-histidine and 3 methyl-histidine, resolution by LC or detection of different optimized product masses allowed accurate quantification of these amino acids.

Quantification of FAA and DPs

Serial dilutions of authentic FAA and DP standards were made with a fixed amount (100 pmol) of five IS. An example of the total ion current (TIC) of authentic FAAs or DPs and extracted SRM of 5 internal standards is shown in FIG. 1A-F. Freshly made stock solutions of FAAs and DPs yielded one major ion while after storage, some standards gave multiple peaks, likely because of oxidation or degradation of the amino acids. The relative retention time of all standards deviated <2.5% relative to the expected retention time or when compared to internal standards for experiments using the same solvent composition and LC gradient. The relationship between the concentrations of each FAA, DP and IS ($[^2H_3]$-L-DOPA, homoarginine, homophenylalanine) were linear for most FAAs and DPs, while standard curves using $[^{15}N]$N-Glutamine and $[^2H_3]$-methionine were linear only for their respective unlabeled amino acids. For most standard curves using $[^2H_3]$-L-DOPA as an IS, the correlation of mole quantities to peak area ratios was linear ($R^2>0.85$) (FIG. 1G, Table 1, columns 6-8). Injection of multiple standards yielded a percentage difference <10% between expected and calculated concentrations for most FAAs and DPs. The limit of detection (LOD) obtained by serial dilution of each standard FAA and DP was in the low pmol level when multiple samples were monitored. This method is sensitive with a LOD for most FAAs and DPs in the 0.05-1 pmol range (Table 1, columns 6-8). The dynamic range (0.01-100 pmol) is 3-5 orders of magnitude for the different metabolites.

FAA and DP Concentrations in CSF, Plasma and Urine

After developing a sensitive method for FAA and DP detection, we applied it to human samples (CSF, plasma and urine). FAAs and DPs in CSF reflect their brain metabolism. Levels of FAAs and DPs in plasma indicate uptake, removal or release en route to the brain and other organs, while the levels in urine represent the removal pathway for FAA metabolites. Using LCMS$^2$ and the isotope dilution strategy, the TIC (FIG. 2A) and several important FAAs were identified in human CSF (FIG. 2). Similarly, examples of several FAAs and DPs detected in plasma and urine are shown in FIG. 3 and FIG. 4, respectively. We quantified 21 FAAs and 2 DPs in CSF, 31 FAAs and 6 DPs in plasma and 23 FAAs and 5 DPs in urine (Table 2).

TABLE 2

| Amino Acids | CSF (nmol/dL) | Plasma (nmol/dL) | Urine (nmol/dL) |
|---|---|---|---|
| 1) Histidine-containing FAAs and DPs | | | |
| Histidine | 1854.17 ± 639.10 | 13049.86 ± 1687.42 | 37263.90 ± 11541.33 |
| 1 Methyl histidine | 402.35 ± 139.98 | 1647.64 ± 356.72 | 38638.63 ± 9239.50 |
| 3 Methyl histidine | 347.45 ± 71.41 | 739.81 ± 153.56 | 27817.89 ± 6739.06 |
| Carnosine | ND | 654.23 ± 100.61 | 18694.81 ± 9996.17 |
| Anserine | ND | 26.63 ± 7.97 | 41893.77 ± 23311.63 |
| 2) Aromatic-containing FAAs | | | |
| Tryptophan | 160.22 ± 36.05 | 2916.74 ± 709.06 | 1661.36 ± 346.69 |
| Phenylalanine | 678.94 ± 79.15 | 7707.78 ± 996.12 | 1763.99 ± 317.26 |
| Tyrosine | 2553.68 ± 270.19 | 16382.48 ± 2310.10 | 13205.55 ± 3295.70 |
| DOPA | ND[1] | 513.01 ± 121.61 | ND |
| Dopamine | 33.67 ± 5.03 | 2219.31 ± 433.48 | ND |
| 3) FAAs involved in the urea cycle or in NO synthesis | | | |
| Arginine | 2183.74 ± 273.39 | 9831.56 ± 625.94 | 2447.29 ± 479.65 |
| Citrulline | 2884.71 ± 292.21 | 10043.02 ± 418.00 | 19848.25 ± 5056.55 |
| Ornithine | ND | 5391.24 ± 2442.10 | 6639.78 ± 1758.87 |
| 4) Glutamate- and proline-derived FAA and DPs | | | |
| Glutamic acid | ND | 2716.21 ± 1032.96 | ND |
| Pyroglutamine | 12.87 ± 1.04 | 32.25 ± 4.98 | 298.64 ± 118.88 |
| γ-Glutamyl-ε-lysine | ND | 13.29 ± 2.65 | ND |
| GABA | ND | 193.01 ± 59.96 | ND |
| βABA | ND | 292.56 ± 51.90 | ND |
| ABA | ND | 2157.76 ± 700.68 | ND |
| DABA | ND | 9848.23 ± 1281.46 | 71953.51 ± 17976.57 |
| Glutamine | 13909.06 ± 1144.36 | 22332.97 ± 3527.70 | 1645.66 ± 553.01 |
| Proline-hydroxyproline | 6.95 ± 1.21 | 906.71 ± 138.32 | 759.49 ± 119.19 |
| 4-Hydroxy Proline | 29.80 ± 3.00 | 568.28 ± 106.97 | 286.74 ± 55.04 |
| Glycyl proline | 8.92 ± 1.21 | 22.98 ± 2.59 | 46.10 ± 9.94 |
| Proline | 32.66 ± 9.82 | NR | ND |
| 5) Aspartate-, serine- and pyruvate-derived FAAs | | | |
| Aspartic acid | ND | 1003.61 ± 265.86 | ND |
| Asparagine | 181.86 ± 31.83 | NR | 235.92 ± 6.53 |
| Isoleucine | 281.43 ± 64.43 | 187810.77 ± 28068.57 | 184.99 ± 84.41 |
| Threonine | ND | NR | 49.52 ± 15.43 |
| Lysine | 5351.34 ± 1462.52 | 18317.00 ± 4875.55 | 13778.29 ± 5757.93 |
| Hydroxy lysine | ND | 51.05 ± 4.36 | ND |
| Lysyl alanine | ND | 127222.47 ± 16481.34 | 513292.77 ± 161435.94 |
| Serine | ND | 21.15 ± 2.74 | ND |
| Cysteine | 131.62 ± 71.03 | 1087.05 ± 225.73 | 2922.35 ± 43.45 |
| Cystine | 693.00 ± 201.88 | 15475.08 ± 3889.80 | 77988.79 ± 16066.00 |
| Cystathionine | ND | 103.34 ± 21.05 | 3028.55 ± 682.19 |
| Glycine | 21.83 ± 7.06 | 15.13 ± 1.10 | 8.53 ± 1.31 |

TABLE 2-continued

| Amino Acids | CSF (nmol/dL) | Plasma (nmol/dL) | Urine (nmol/dL) |
|---|---|---|---|
| Valine | 539.44 ± 158.45 | 5197.60 ± 1372.70 | 1828.19 ± 483.91 |
| Leucine | 1281.14 ± 174.84 | NR | 1176.95 ± 315.86 |
| Allo-leucine | ND | 3450.96 ± 584.46 | ND |
| Aminopimelic acid | ND | 245.30 ± 55.20 | ND |

[1]ND, not detected; NR, not resolved

Under conditions where a particular FAA or DP was not resolved or not detected in a specific body fluid, increasing the amount of fluid used or changing the LC conditions improved detection. For example, although we did not clearly integrate and measure dopamine in CSF, peaks with S/N>2 can be obtained by doubling the amount of CSF used in our studies. Therefore, more FAA and DPs can be detected by increasing our sample load for CSF, plasma or urine. Alternatively, sensitivity can be improved for a specific metabolite by increasing the scan time or decreasing the number of metabolites measured per scan. The values of many of the FAA measured by LCMS$^2$ were similar to those measured by ionic exchange chromatography (Molina et al., 1998) or were in the range of published values. Any discrepancies in concentrations may be because of differences in the methods for quantification or in the ages of the study participants. Regardless, these data show that quantitative levels of many FAAs and DPs can be obtained using differentially labeled stable isotope standards.

Comparison of FAA and DPs in Body Fluids

To aid interpreting the data presented here, we will divide and discuss our data based on functional or biochemical properties that include: 1) Histidine (imidazole)-containing FAAs or DPs that have antioxidant properties. 2) Aromatic-containing FAAs that are neurotransmitters. 3) FAAs and DPs associated with urea metabolism/detoxification and NO formation. 4) Glutamate- and proline-derived FAAs and DPs. 5) Aspartate-, serine and pyruvate-derived FAAs.

The major histidine-containing FAAs and DPs are histidine, 1-methyl-histidine, 3-methyl-histidine, carnosine and anserine (Table 2). For most of these compounds, the concentration was highest in urine>plasma>CSF.

Tryptophan, phenylalanine, tyrosine, L-DOPA and dopamine were the major aromatic-containing FAA measured in CSF, plasma or urine (Table 2). Concentrations of these FAAs were highest in the plasma>urine>CSF.

Arginine, citrulline and ornithine were the major FAAs associated with urea metabolism and NO synthesis detected in CSF, plasma or urine. The concentration gradient was urine>plasma>CSF except arginine that was highest in plasma (Table 2).

Several FAAs derived from glutamate metabolism were detected in CSF, plasma and urine. Aspartate-derived FAAs (asparagine, threonine, isoleucine and lysine), serine derived FAAs (cysteine, glycine) and pyruvate-derived FAAs (valine, leucine) were detected in CSF, plasma or urine. Lysine concentration was highest of the aspartate-derived FAAs in CSF (Table 2).

Together, these data show that many FAAs and DPs can be measured in body fluids and the concentration gradient between body fluids is different for amino acid biochemical groups.

Example 2

This shows free amino acid and/or dipeptide changes in the body fluids from Alzheimer's disease subjects.

Materials and Methods

All reagents, solvents, amino acid standards, dipeptide standards, deuterated internal standards, protein dye reagent concentration and the C18 liquid chromatography column were as described in Example 1.

We recruited AD patients ("pAD") and Control ("CT") study participants prospectively from the North Los Angeles area for our IRS-approved research. We obtained informed consent from each study participant and all procedures complied with the Privacy of Personal Health Information Act and the Declaration of Helsinki principles for the use of human subjects in research. A neurologist obtained a complete medical history for each participant using a structured interview. A neuropsychologist administered a battery of cognitive assessments including the MMSE and ADAS-cog tests (Mendiondo et al., 2000; Weyer et al., 1997) to decide mental and cognitive deficits that fulfilled the criteria for pAD. We used guidelines approved by the American Academy of Neurology and the AMA for inclusion and exclusion criteria (Knopman et al., 2001) and the designation of probable AD is based on clinical criteria proposed by the Department of Health and Human Services Task Force on Alzheimer's Disease (McKhann et al., 1984). In the pAD group, all participants had a history of progressive dementia of more than 12 months duration, had impairment of memory plus 2 or more areas of cognition, had no disturbance of consciousness and had disease onset between ages 40 and 90. We excluded pAD participants who had symptoms of clinical stroke, systemic disorders or other brain diseases that could account for the progressive deficits in memory and cognition. We also excluded participants if they had infection, fever, bleeding disorder, treatment, and other acute medical conditions that precluded lumbar puncture. Age- and gender-matched control subjects had no classifiable brain disorder after complete neurological and psychiatric evaluation. Comorbid conditions such as hypertension were recorded but were not a reason for exclusion.

Participants were not excluded from this study if they were taking prescription medications. However, a careful record of all prescription medications was kept. Of the 16 study participants included in this study, 7 pAD subjects were on a reversible acetylcholinesterase inhibitor, 2 CT and 4 pAD subjects were on selective serotonin reuptake inhibitors (SSRI), 3 CT and 3 pAD women were on estrogen replacement therapy, and 3 pAD subjects were on K$^+$/Na$^+$ blockers. Other prescription drugs included antihistamines (2 CT, 1 pAD), Ca$^{2+}$ channel blocker (1 CT, 1 pAD), 5HT1 receptor antagonist (2 pAD), alpha1 adrenergic blocker (2 pAD), cysteinyl leukotriene receptor inhibitor (1 CT), hydroxymethyl-glutaryl-coenzyme A reductase inhibitor (1 pAD) and a selective cyclooxygenase inhibitor (1 pAD).

We collected CSF by lumbar punctures, whole blood by venipuncture and midstream urine as described (Fonteh et al., 2006). We stored all samples in aliquots at −80° C. until needed for analysis.

A micro titer plate-based Coomasie protein assay using bovine serum albumin (0-100 μg/ml) as standard was used to measure protein concentrations (Zuo and Lundahl, 2000). Briefly, 20 μl of diluted CSF (20×), diluted plasma (500×) and urine (1×) were added to 96 well micro titer plate in triplicates. Coomassie dye (BioRad, Hercules, Calif.) was diluted (5×) and 200 μl added to each well. After 5 min, the OD at 595 nm was obtained using a microplate reader (Molecular Devices, Sunnyvale, Calif.) and protein concentrations in each sample determined using Softmax software (Molecular Devices).

Solid phase extraction followed by a derivatization (Husek, 1998) procedure using the EZ-Faast amino acid analyses kit from Phenomenex was performed on samples from CT and pAD subjects as described in Example 1. Precursor ions of FAA and DPs and selected reaction monitoring (SRM) parameters (collision energy and tube lens voltage) were optimized for each FAA and DP (Fonteh et al., 2006). LCMS$^2$ was then performed and concentrations of FAA and DPs determined in CSF, plasma and urine from CT and pAD subjects.

Data are presented as the mean±SEM and comparisons are made between CT and pAD. We used Prism (GraphPad Software, San Diego, Calif.) for graphical presentation and Statview (Abacus Concepts, Berkeley, Calif.) to compare the concentrations of FAAs and DPs using a t-test for unpaired data and the Mann Whitney tests where appropriate. P values less than 0.05 were considered significant.

Results

Clinical Classification and Protein Concentrations

Biochemical studies involving human subjects are often complex because of clinical heterogeneity. Our immediate goal was to identify changes in FAA and DP concentrations in a selected age- and gender-matched CT and pAD cohort. Our long-term goal is study these identified biochemical pathways in a larger sample size that would include pAD classification based on disease severity to better dissect disease-specific changes. In these first studies, 16 gender- and aged-matched study participants were recruited. As shown on Table 3, there was no significant difference in the mean age of the pAD and the CT group. Also, no age differences were found between gender groups (data not shown). A battery of neuropsychological tests that included MMSE and ADAS-Cog complemented neurological examination and diagnosis. Mean MMSE score of the pAD study participants was significantly lower than that of the CT group (Table 3). Mean ADAS-Cog score of the pAD group was significantly higher than that of the CT group (Table 3). The mean±SEM and the p value obtained using a student's t-test for unpaired data are shown for each variable.

TABLE 3

| Parameters | CT (n = 8) | pAD (n = 8) | p value |
|---|---|---|---|
| Age (years) | 79.500 + 1.927 | 77.875 + 2.601 | 0.6235 |
| MMSE | 29.000 + 0.463 | 11.375 + 3.173 | <0.0001* |
| ADAS-COG | 6.320 + 1.325 | 43.079 + 8.543 | 0.0008* |
| CSF Protein (mg/ml) | 0.426 + 0.032 | 0.413 + 0.043 | 0.8125 |
| Plasma Protein (mg/ml) | 120.125 + 2.386 | 118.362 ± 6.198 | 0.7946 |
| Urine Protein (mg/ml) | 0.088 + 0.012 | 0.135 + 0.026 | 0.1295 |

(*p < 0.05)

As part of the clinical evaluation, we recorded prescription drug use. pAD participants (3.5±1.4 prescriptions) were more likely (p=0.012) to be taking prescription medication than CT subjects (1.1±0.8 prescriptions). Acetylcholinesterase inhibitors, serotonin inhibitors and antihypertensives accounted for most prescription drugs taken by pAD subjects. These initial studies show that one can distinguish pAD from CT subjects based on neuropsychological scores and as expected, pAD subjects take more prescription medications than CT subjects.

We next determined the protein concentrations in CSF, plasma and urine. Although the mean protein levels in CSF and plasma were slightly lower in pAD than control subjects, these were not statistically different between the two groups (Table 1). The mean concentration of protein in urine was 53.4% higher in pAD subjects but this was not significantly different from that of CT subjects and was not associated with increased plasma urea. There were no gender differences in the mean protein concentrations for CT or pAD subjects (data not shown). These studies suggest the protein intake and excretion of our study groups are similar.

FAA and DP Concentrations in CSF, Plasma and Urine

Using LCMS$^2$ with isotope dilution, we identified several important FAAs in human body fluids from subjects without any known neurological disease (CT). We quantitatively measured 21 FAAs and 2 DPs in CSF, 31 FAAs and 6 DPs in plasma and 23 FAAs and 5 DPs in urine. Table 4 provides the FAA and DP concentrations in pAD samples. These data are mean±SEM of 8 pAD subjects (4 male and 4 female) with an average age of 79.5+1.93 years.

TABLE 4

| Amino Acids | CSF (nmol/dL) | Plasma (nmol/dL) | Urine (nmol/dL) |
|---|---|---|---|
| Histidine | 1440.62 ± 632.90 | 11668.00 ± 1815.72 | 46379.50 ± 6615.54 |
| 1 Methyl histidine | 259.86 ± 113.27 | 1066.92 ± 268.21 | 23879.40 ± 6141.94 |
| 3 Methyl histidine | 247.66 ± 157.80 | 516.08 ± 127.07 | 36759.65 ± 2580.93 |
| Carnosine | ND | 328.40 ± 91.30 (*) | 28603.29 ± 15669.25 |
| Anserine | ND | 45.70 ± 21.49 | 12116.43 ± 7884.92 |
| Tryptophan | 139.31 ± 32.35 | 3306.352 ± 899.580 | 1803.15 ± 355.75 |
| Phenylalanine | 591.10 ± 79.50 | 7177.74 ± 921.45 | 2076.10 ± 279.78 |
| Tyrosine | 2718.74 ± 483.68 | 14377.43 ± 1549.44 | 16025.73 ± 2308.09 |
| DOPA | ND | 1400.84 ± 253.68 (*) | ND |
| Dopamine | 34.823 ± 10.298 | 1802.84 ± 245.52 | ND |
| Arginine | 616.98 ± 145.91 | 9134.37 ± 1310.35 | 3161.76 ± 313.76 |
| Citrulline | 2737.28 ± 264.50 | 9497.67 ± 1118.66 | 32351.72 ± 4352.72 |
| Ornithine | ND | 6835.01 ± 2243.52 (+) | 18749.52 ± 7706.66 |
| Glutamic acid | NR | 3318.85 ± 1126.55 | NR |
| Pyroglutamine | 8.85 ± 2.43 | 26.12 ± 2.37 | 253.55 ± 74.53 |
| γ-Glutamyl-ϵ- | ND | 16.29 ± 3.92 | ND |

TABLE 4-continued

| Amino Acids | CSF (nmol/dL) | Plasma (nmol/dL) | Urine (nmol/dL) |
|---|---|---|---|
| lysine | | | |
| GABA | ND | 184.11 ± 21.59 | ND |
| βABA | ND | 272.15 ± 50.28 | ND |
| ABA | ND | 1979.45 ± 217.41 | ND |
| DABA | ND | 11635.85 ± 999.12 | 55181.11 ± 7696.82 |
| Glutamine | 114661.24 ± 1066.76 | 22834.59 + 1197.97 | 1772.45 ± 738.34 |
| Proline-hydroxyproline | 8.63 ± 2.02 | 999.32 ± 139.45 | 1512.15 ± 296.02 |
| 4-Hydroxy Proline | 28.51 ± 5.57 | 566.39 ± 67.36 | 329.69 ± 26.35 |
| Glycyl proline | 8.66 ± 1.57 | 23.18 ± 3.80 | 53.76 ± 8.89 |
| Proline | 68.60 ± 35.57 | NR | ND |
| Aspartic acid | ND | 1267.54 ± 286.01 | ND |
| Asparagine | 177.66 ± 16.02 | NR | 405.57 ± 70.32 |
| Isoleucine | 240.97 ± 65.57 | 149515.99 ± 37297.20 | 200.34 ± 65.51 |
| Threonine | ND | NR | 38.348 ± 4.939 |
| Lysine | 4464.69 ± 1084.58 | 21677.07 ± 5450.43 | 8381.49 ± 2649.70 |
| Hydroxy lysine | ND | 50.45 ± 2.88 | ND |
| Lysyl alanine | ND | 113839.27 ± 24960.53 | 532952.54 ± 63321.17 |
| Serine | ND | 21.18 ± 2.43 | ND |
| Cysteine | 130.14 ± 64.05 | 1281.97 ± 217.90 | 3043.92 ± 573.25 |
| Cystine | 784.14 ± 249.21 | 20920.33 ± 4593.49 | 109491.95 ± 18221.10 |
| Cystathionine | ND | 103.15 ± 22.15 | 2557.881 ± 752.357 |
| Glycine | 28.967 ± 12.291 | 15.25 ± 1.12 | 15.55 ± 1.66 (*) |
| Valine | 413.27 ± 122.09 | 5826.51 ± 1474.97 | 1119.59 ± 189.07 |
| Leucine | 1145.55 ± 151.30 | NR | 1379.89 ± 171.70 |
| Allo-leucine | ND | 4439.66 ± 962.29) | ND |
| Aminopimelic acid | ND | 216.45 ± 47.07 | ND |

ND, not detected; NR, not resolved;
(*) p < 0.05 compared to aged and gender-matched controls.

To determine changes in FAA and DP metabolism, we compared these metabolites between gender- and aged-matched subjects with pAD and CT. Table 5 provides changes in FAA and DP concentrations in pAD samples. Changes are calculated by comparing the mean concentration of FAA and DPs in pAD (n=8) compared to pAD (n=8). These results are also shown in FIG. 5.

TABLE 5

| Amino Acids | CSF (Change, % CT) | Plasma (Change, % CT) | Urine (Change, % CT) |
|---|---|---|---|
| Histidine | −22.30 | −10.59 | 24.46 |
| 1 Methyl histidine | −35.42 | −35.25 | −38.20 |
| 3 Methyl histidine | −28.72 | −30.24 | 32.14 |
| Carnosine | ND | −49.80* | 53.00 |
| Anserine | ND | 71.64 | −71.08 |
| Tryptophan | −13.05 | 13.36 | 8.56 |
| Phenylalanine | −12.93 | −6.87 | 17.69 |
| Tyrosine | 6.46 | −12.24 | 21.36 |
| DOPA | ND | 173.06* | ND |
| Dopamine | 3.36 | −18.77 | ND |
| Arginine | −15.79 | −7.10 | 29.19 |
| Citrulline | −5.11 | −5.43 | 63.0 |
| Ornithine | ND | 26.78 | 182.38 |
| Glutamic acid | NR | 22.19 | NR |
| Pyroglutamine | −15.27 | −21.44 | −15.10 |
| γ-Glutamyl-ε-lysine | ND | 22.60 | ND |
| GABA | ND | −4.62 | ND |
| βABA | ND | −6.98 | ND |
| ABA | ND | −8.26 | ND |
| DABA | ND | 18.15 | −23.31 |
| Glutamine | 5.41 | 2.25 | 7.70 |
| Proline-hydroxyproline | 24.21 | 10.21 | 50.94 |
| 4-Hydroxy Proline | −4.35 | −0.33 | 14.97 |
| Glycyl proline | −2.93 | 0.86 | 16.62 |
| Proline | 110.03 | NR | ND |
| Aspartic add | ND | 26.30 | ND |
| Asparagine | −2.31 | NR | 71.91 |
| Isoleucine | −14.38 | 20.39 | 8.30 |
| Threonine | ND | NR | −22.55 |
| Lysine | −16.57 | 18.32 | −40.04 |
| Hydroxy lysine | ND | −1.19 | ND |
| Lysyl alanine | ND | −10.52 | 3.83 |
| Serine | ND | 0.15 | ND |
| Cysteine | −1.12 | 17.93 | 4.16 |
| Cystine | 14.69 | 35.19 | 40.39 |
| Cystathionine | ND | 0.19 | −15.54 |
| Glycine | 32.67 | 1.44 | 82.43* |
| Valine | −23.39 | 12.10 | −38.76 |
| Leucine | −10.58 | NR | 17.24 |
| Allo-leucine | ND | 28.64 | ND |
| Aminopimelic acid | ND | −11.76 | ND |

ND, not detected; NR, not resolved;
*p < 0.05 compared with aged and gender-matched CT.

To aid the interpretation, these are divided into biochemical or functional families to include: 1) Histidine (imidazole)-containing FAAs or DPs that have antioxidant properties. 2) Aromatic-containing FAAs that are neurotransmitters. 3) FAAs and DPs associated with urea metabolism/detoxification and NO formation. 4) Glutamate-derived FAAs and DPs, 5) Aspartate and serine-derived FAAs. Results outlining differences in these FAA families in CT and pAD samples are described below.

Concentration of Histidine-Containing FAAs and DPs

Figure 6:
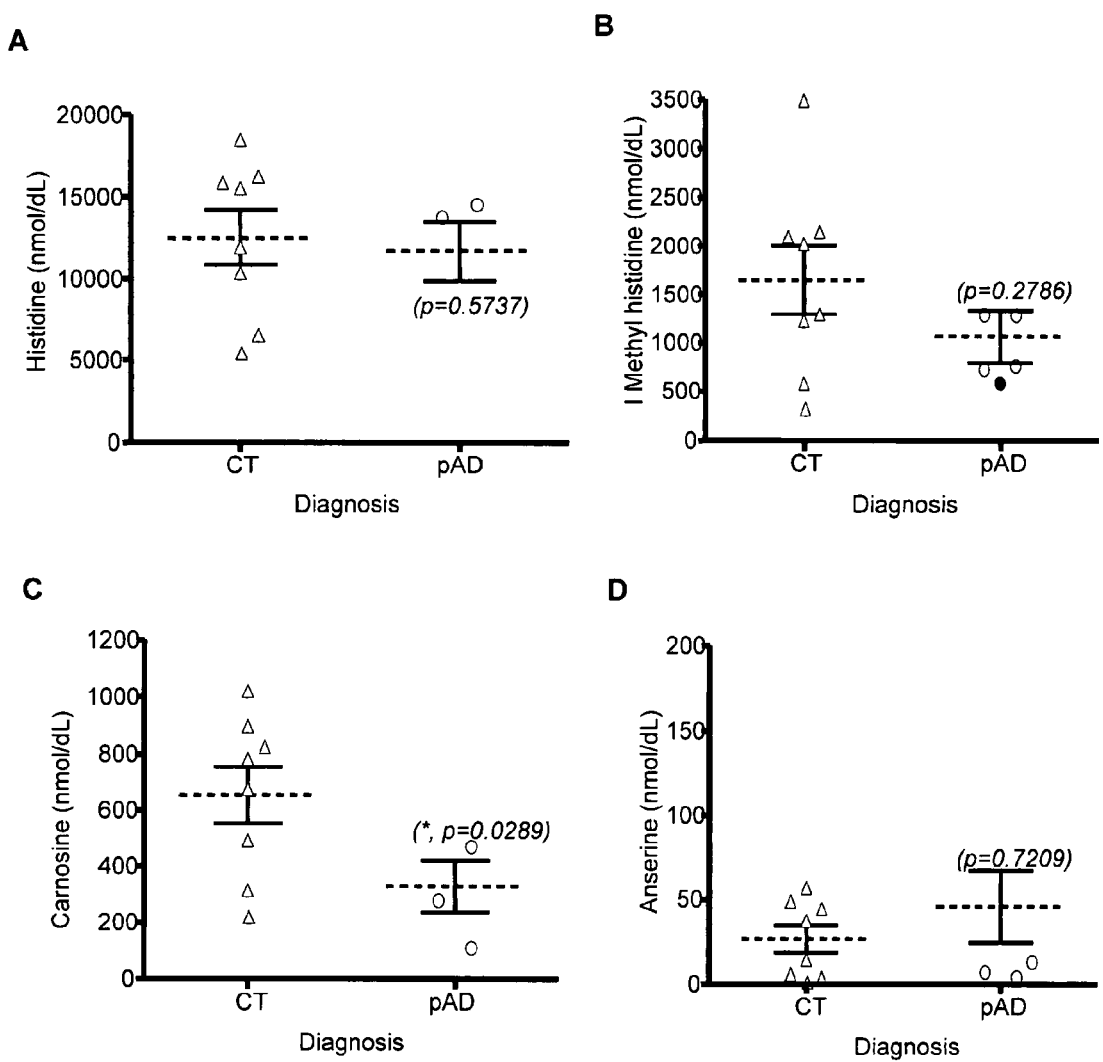
FIGS. 6A-D show concentrations of histidine (6A), 1-methyl histidine (6B), carnosine (6C), and anserine (6D) in plasma from age- and gender-matched control and AD patients as determined using LCMS². These data are individual plasma concentrations of control (n=8) and AD patients (n=8) subjects, with the mean concentrations (dotted line)±SEM. P values are shown for each plot (*, p<0.05).

In CSF from pAD subjects, the concentration of histidine-containing FAAs were lower than that of CT subjects (FIG. 5). Although not significant, the mean concentration of histidine (FIG. 6A) and methyl-histidine (FIG. 6B) were lower in pAD plasma. The mean concentration of the DP, carnosine was significantly lower (p=0.0289) in pAD than in CT (FIG. 6C). The mean concentration of another DP, anserine, was 71% higher in pAD plasma than CT (FIG. 6D). However, the combined DP concentration was still significantly lower (p=0.0246) in pAD than CT plasma.

In urine, histidine, 3-methyl-histidine and carnosine concentrations were higher in pAD than CT (FIG. 5). In contrast, 1-methyl-histidine and anserine concentrations were lower in pAD urine. Total histidine and methyl-histidine concentration was higher in pAD urine while total carnosine and anserine concentrations were lower in pAD than CT. Together, these data suggest that precursors of carnosine and anserine are lower in CSF and plasma, concomitant with a decrease in total DP concentration. Female study participants accounted for most of the decrease in plasma carnosine concentration (data not shown). There is increased urinary excretion of histidine-containing FAAs in pAD, perhaps a clearance from the degenerating brain. However, we need further research to validate and define the precise cause of these changes in CSF and plasma.

Concentration of Aromatic-Containing FAAs

Figure 7:
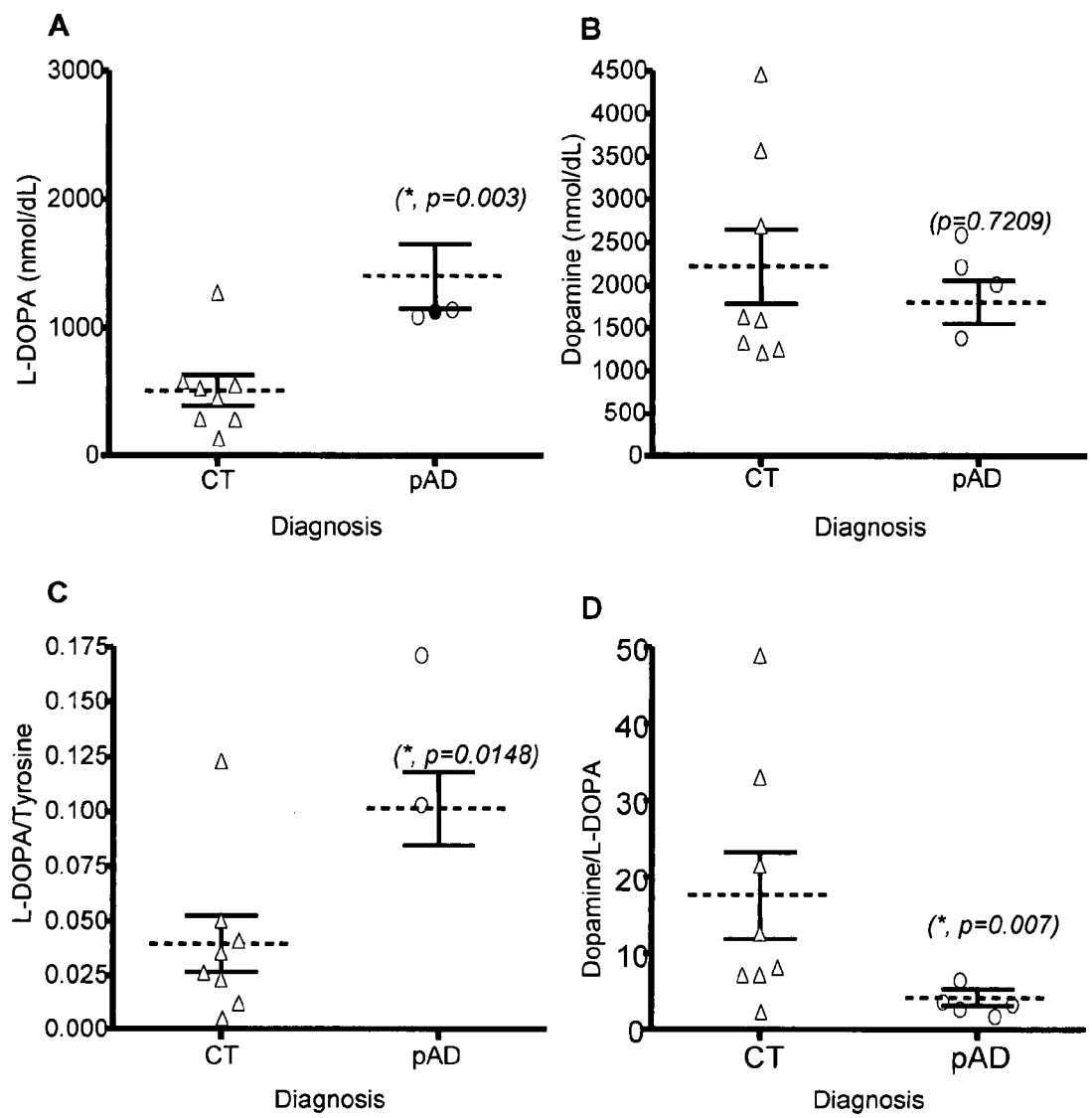
FIGS. 7A-D show concentrations of L-DOPA (7A), dopamine (7B), and the ratios of L-DOPA/tyrosine (7C) and dopamine/L-DOPA (D) in plasma from age-matched CT and AD patients determined using LCMS². These data are concentrations of control (n=8) and AD patients (n=8), with the mean concentration (dotted line)±SEM. P values are shown for each plot (*, p<0.05).

Tryptophan, phenylalanine, tyrosine, L-DOPA and dopamine were the major aromatic-containing FAA measured in CSF, plasma or urine (FIG. 5). In CSF, there was no significant difference between CT and pAD concentrations of aromatic FAAs (FIG. 5). While tryptophan, tyrosine and phenylalanine concentrations in plasma were not altered in pAD (FIG. 5), mean plasma L-DOPA concentration was significantly higher (p=0.003) in pAD than CT (FIG. 7A). In contrast, the mean dopamine concentration was lower in pAD than in CT plasma (FIG. 7B). The ratio of L-DOPA to tyrosine was significantly higher in pAD than CT (FIG. 7C) while the mean dopamine to L-DOPA ratio was significantly lower in pAD (FIG. 7D). These differences in enzyme substrate and product ratios suggest there are changes in tyrosine hydrolase and L-DOPA decarboxylase activities in pAD. Only small changes in aromatic FAA concentrations were found in urine (FIG. 5), although we were not able to measure urinary L-DOPA and dopamine in these experiments. Together, these data show changes in peripheral dopamine biosynthesis in pAD subjects likely credited to enzymes in the dopamine biosynthetic pathway.

FAAs Involved in Urea Metabolism and NO Synthesis

CSF arginine and citrulline concentrations were slightly lower in CSF from pAD (FIG. 5). Total arginine and citrulline was highest in CSF from CT_M (6,092.77±472.47 nmol/dL) and this was significantly higher (p=0.0086) than the concentration in CT_F (4044.15±249.83 nmol/dL). CT and pAD difference for males (1,972.99 nmol) was ~23 fold higher than the difference for females (83.16 nmol). In plasma, ornithine was 26.8% more abundant in pAD than in CT while the other FAAs are were not altered (FIG. 5). In contrast to the CSF and plasma, urine arginine, citrulline and ornithine concentrations were all higher in pAD than CT (FIG. 5). Total concentration of these FAAs was significantly (p=0.0109) higher in pAD (54,262.90±5,757.35 nmol/dL) than CT (28.94±6.44 nmol/dL). These data suggest that male subjects account for the differences in urea metabolism or NO synthesis in CSF, while differences in urine are not gender-dependent.

Glutamate Metabolism

Of the many glutamate-derived FAAs detected in CSF, plasma and urine, only slight changes were found in pAD (FIG. 5). Concentrations of several proline-containing amino acids were increased in pAD urine. These data show there may be differences in proline metabolism but not in other glutamate-derived metabolites in pAD.

Aspartate and Serine Family of FAA

In CSF, only modest differences between CT and pAD samples were noted in the concentrations of aspartate- and serine derived FAAs (FIG. 5). In plasma, isoleucine, lysyl alanine, lysine and cysteine were the highest concentration of FAAs or DP from the aspartate or serine families. Compared with CT plasma, few differences were observed in the concentrations of these compounds except for aspartic acid, cysteine and alloleucine, which were more than 25% higher in pAD (FIG. 5). In urine, there was an increase in asparagine, cysteine and glycine and a decrease in lysine and valine levels in pAD. Although urine glycine concentrations were lower than those of other FAAs, it increased significantly (p<0.0054) in pAD (15.6±1.7 nmol/dL) compared with CT (8.5±1.3 nmol/dL). Together, these data show the metabolism of aspartate or serine-derived FAAs is not altered in CSF or plasma while excretion of glycine in urine is higher in pAD than CT.

Discussion

Using $LCMS^2$ on age and gender-matched samples, we have revealed several new insights into FAA biochemical pathways in AD. The concentrations of FAAs or DPs involved in antioxidation (carnosine), neurotransmission (L-DOPA and dopamine), urea cycle/detoxification or NO formation (arginine, citrulline, ornithine) and inhibitory FAA (glycine) are significantly altered in samples from pAD compared with CT. Together, these data show the importance of FAAs and DPs in pAD pathogenesis and provide a scientific reason for designing novel strategies to control FAA metabolism in AD patients.

The influence of prescription drugs on changes in FAA and DP concentrations has been considered. In the present study, pAD participants took >2× more prescription drugs than CT. A careful review of the literature and known modes of drug action does not suggest that these classes of prescription medications are likely to influence any of the biochemical pathways involving the FAAs and DPs described below.

The concentration of FAAs and DPs in CSF or plasma will be dictated in part by how much protein one consumes and by metabolic processes that control the absorption, transport, degradation and excretion of these molecules. Similarly, concentrations of FAAs and DPs in urine will be influenced by the rate of excretion of these molecules. These processes have significant ramifications on human health since FAAs and DPs control processes ranging from neurotransmission by receptor-mediated signaling, prevention of oxidation and detoxification by urea excretion. In this study, the protein concentrations of plasma, CSF or urine are only slightly different between CT and pAD study participants. If uptake does not contribute significantly to differences between CT and pAD, it is likely that proteolysis, deamination and other biochemical reactions that control FAA may be important. Given the increase in protein concentration in urine from pAD in this age- and gender-matched sample when none of the subjects had high urea or creatine on routine blood testing, it is likely there is increased degradation of proteins in AD. This would not be surprising because of the overall loss of brain tissue in AD.

Overall, the strength of $LCMS^2$ in clarifying complex biochemical pathways is illustrated. FAAs or DPs that are altered in pAD may serve as metabolic markers or metabolic risk factors.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A method of diagnosing Alzheimer's disease ("AD") in an individual, comprising:
   a) measuring the level of at least one AD diagnosis marker in a biological fluid sample from the individual by chromatography tandem mass spectrometry,
   b) comparing the level of at least one AD diagnosis marker in the biological fluid sample from the individual with a reference level, and
   c) determining whether the individual has AD based on a characteristic change in the level of at least one AD diagnosis marker,
   wherein at least one AD diagnosis marker is carnosine.

2. The method of claim 1, comprising measuring the levels of at least three AD diagnosis markers in the individual and comparing with reference levels, wherein at least one AD diagnosis marker is carnosine, at least one AD diagnosis marker is an aromatic-containing free amino acid, and at least one AD diagnosis marker is a glutamate-derived free amino acid or dipeptide.

3. The method of claim 1, comprising measuring the levels of at least two AD diagnosis markers in the individual and comparing with reference levels.

4. The method of claim 3, comprising measuring the levels of at least five AD diagnosis markers in the individual and comparing with reference levels.

5. The method of claim 4, comprising measuring the levels of at least ten AD diagnosis markers in the individual and comparing with reference levels.

6. The method of claim 1, wherein the biological fluid comprises cerebrospinal fluid (CSF).

7. The method of claim 1, wherein the biological fluid comprises plasma.

8. The method of claim 1, wherein the biological fluid comprises urine.

9. The method of claim 1, wherein an increase in the level of carnosine is indicative of AD.

10. The method of claim 9 wherein the biological fluid comprises urine.

11. The method of claim 1 wherein a decrease in the level of carnosine is indicative of AD.

12. The method of claim 11 wherein the biological fluid comprises plasma.

13. The method of claim 1, wherein the chromatography tandem mass spectrometry is liquid chromatography tandem mass spectrometry.

14. A method of assessing changes in levels of at least two markers in a biological body fluid sample, comprising measuring the levels of the markers in the sample by chromatography tandem mass spectrometry and comparing the measured levels with reference levels, wherein the markers are free amino acids or dipeptides, wherein at least one marker is carnosine, and wherein a change in levels of one or more of the free amino acids or dipeptides is indicative of AD.

15. The method of claim 14, wherein the levels of at least five free amino acids or dipeptides are detected.

16. The method of claim 1, wherein the method further comprises extracting free amino acids or dipeptides from the biological fluid sample.

17. The method of claim 16, wherein the method further comprises subjecting the free amino acids or dipeptides to derivatization prior to measuring the level of at least one AD diagnosis marker in the biological fluid sample.

18. The method of claim 1, wherein the step of measuring the level of at least one AD diagnosis marker comprises selective reaction monitoring (SRM) following the chromatography tandem mass spectrometry.

19. The method of claim 14, wherein the chromatography tandem mass spectrometry is liquid chromatography tandem mass spectrometry.

20. The method of claim 14, wherein the biological fluid sample comprises cerebrospinal fluid (CSF).

21. The method of claim 14, wherein the biological fluid sample comprises plasma.

22. The method of claim 14, wherein the biological fluid sample comprises urine.

* * * * *